United States Patent
Wei et al.

(10) Patent No.: US 10,076,661 B2
(45) Date of Patent: *Sep. 18, 2018

(54) CONDITIONAL ELECTRICAL STIMULATION

(71) Applicant: Medtronic, Inc., Minneapolis, MN (US)

(72) Inventors: Xuan K. Wei, Minnetonka, MN (US); Eric H. Bonde, Minnetonka, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/390,168

(22) Filed: Dec. 23, 2016

(65) Prior Publication Data
US 2017/0173327 A1    Jun. 22, 2017

Related U.S. Application Data

(63) Continuation of application No. 13/237,216, filed on Sep. 20, 2011, now Pat. No. 9,561,366, which is a (Continued)

(51) Int. Cl.
*A61N 1/36* (2006.01)

(52) U.S. Cl.
CPC ..... *A61N 1/36007* (2013.01); *A61N 1/36107* (2013.01); *A61N 1/36139* (2013.01); *A61N 1/36175* (2013.01); *A61N 1/36178* (2013.01)

(58) Field of Classification Search
CPC .............. A61N 1/3605; A61N 1/36107; A61N 1/36175
See application file for complete search history.

(56) References Cited

U.S. PATENT DOCUMENTS 6,606,517 B1 * 8/2003 Park .................... A61N 1/3622
607/14
7,415,308 B2  8/2008 Gerber et al.
(Continued)

FOREIGN PATENT DOCUMENTS

EP           1163928 A2    12/2001
WO       2010111321 A3     9/2010
(Continued)

OTHER PUBLICATIONS

Michelsen HB et al., "A prospective, randomized study: switch off the sacral nerve stimulator during the night?," Dis Colon Rectum, May 2008; 51(5): 538-40, Epub Feb. 26, 2008 (abstract).
(Continued)

*Primary Examiner* — Eric D. Bertram
(74) *Attorney, Agent, or Firm* — Shumaker & Sieffert, P.A.

(57) ABSTRACT

In general, the disclosure describes techniques for providing conditional electrical stimulation to a patient for pelvic health. An implantable medical device (IMD) may adjust the delivery cycle of the electrical stimulation applied to a patient in response to receiving a delivery cycle parameter associated with one or more of the following: a time in a time schedule, a control device output from a control device, and physiological information from a physiological information sensing device. As an example, the IMD may monitor a status of one or more inputs of the IMD and adjust the delivery cycle of the electrical stimulation applied to the patient based on the status of the input(s).

23 Claims, 19 Drawing Sheets

Related U.S. Application Data continuation-in-part of application No. PCT/US2010/028406, filed on Mar. 24, 2010, which is a continuation-in-part of application No. PCT/US2010/028400, filed on Mar. 24, 2010, which is a continuation-in-part of application No. PCT/US2010/028396, filed on Mar. 24, 2010.

(60) Provisional application No. 61/164,222, filed on Mar. 27, 2009, provisional application No. 61/164,225, filed on Mar. 27, 2009, provisional application No. 61/164,232, filed on Mar. 27, 2009.

(56) References Cited

U.S. PATENT DOCUMENTS

| | | | |
|---|---|---|---|
| 7,522,061 B2 | 4/2009 | Rondoni et al. | |
| 7,672,728 B2 | 3/2010 | Libbus | |
| 7,769,460 B2 | 8/2010 | Gerber et al. | |
| 7,769,464 B2 | 8/2010 | Gerber et al. | |
| 7,809,443 B2 | 10/2010 | Giftakis et al. | |
| 7,962,220 B2 | 6/2011 | Kolafa et al. | |
| 8,571,666 B2* | 10/2013 | Urmey | A61N 1/36021 607/46 |
| 9,561,366 B2 | 2/2017 | Wei et al. | |
| 2003/0100930 A1 | 5/2003 | Cohen et al. | |
| 2006/0020225 A1 | 1/2006 | Gerber et al. | |
| 2006/0020297 A1 | 1/2006 | Gerber et al. | |
| 2006/0122660 A1* | 6/2006 | Boveja | A61N 1/36007 607/40 |
| 2006/0161217 A1 | 7/2006 | Jaax et al. | |
| 2006/0190051 A1 | 8/2006 | Gerber et al. | |
| 2007/0027494 A1 | 2/2007 | Gerber | |
| 2007/0027495 A1 | 2/2007 | Gerber | |
| 2007/0060967 A1 | 3/2007 | Strother et al. | |
| 2007/0100387 A1 | 5/2007 | Gerber | |
| 2007/0150006 A1 | 6/2007 | Libbus et al. | |
| 2007/0179559 A1 | 8/2007 | Giftakis et al. | |
| 2007/0255374 A1 | 11/2007 | Kolafa et al. | |
| 2008/0208287 A1* | 8/2008 | Palermo | A61N 1/0452 607/48 |
| 2008/0269812 A1 | 10/2008 | Gerber et al. | |
| 2008/0281381 A1 | 11/2008 | Gerber et al. | |
| 2008/0300449 A1 | 12/2008 | Gerber et al. | |
| 2008/0300651 A1 | 12/2008 | Gerber et al. | |
| 2009/0036940 A1 | 2/2009 | Wei et al. | |
| 2009/0083070 A1* | 3/2009 | Giftakis | A61N 1/36132 705/2 |
| 2009/0228067 A1* | 9/2009 | Boyd | A61N 1/0512 607/48 |
| 2012/0010680 A1 | 1/2012 | Wei et al. | |

FOREIGN PATENT DOCUMENTS

| | | |
|---|---|---|
| WO | 2010111324 A1 | 9/2010 |
| WO | 2010111329 A1 | 9/2010 |

OTHER PUBLICATIONS

International Search Report from International Application No. PCT/US2010/028400, dated Jun. 4, 2010, 5 pp.
International Preliminary Report on Patentability from International Application No. PCT/US2010/028400, dated Sep. 27, 2011, 8 pp.
International Search Report from International Application No. PCT/US2010/028396, dated Aug. 18, 2010, 7 pp.
International Preliminary Report on Patentability from International Application No. PCT/US2010/028396, dated Sep. 27, 2011, 5 pp.
International Search Report from International Application No. PCT/US2010/028406, dated Jun. 15, 2010, 4 pp.
International Preliminary Report on Patentability from International Application No. PCT/US2010/028406, dated Sep. 27, 2011, 5 pp.
Prosecution History from U.S. Appl. No. 13/237,216, from Mar. 25, 2013 through Sep. 23, 2016, 154 pp.

* cited by examiner

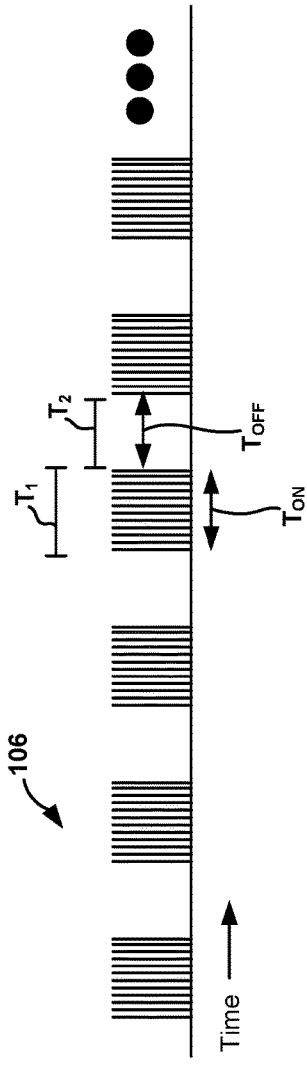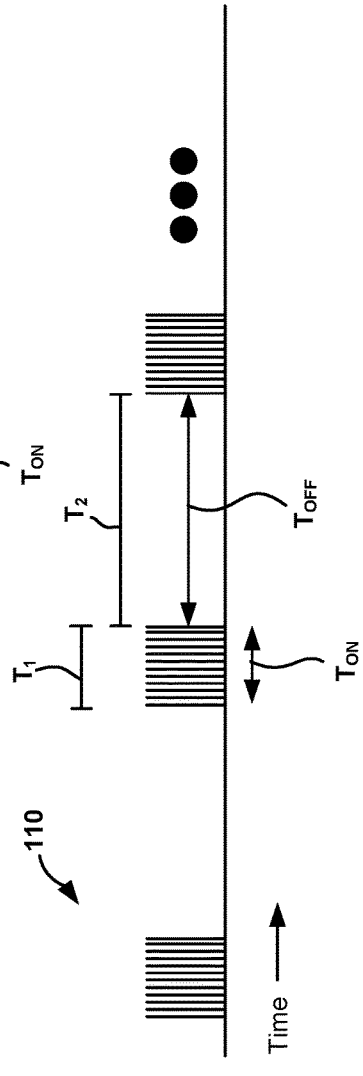
FIG. 9  FIG. 10  FIG. 11

CONDITIONAL ELECTRICAL STIMULATION

RELATED APPLICATIONS

This application is a continuation of U.S. patent application Ser. No. 13/237,216, now U.S. Pat. No. 9,561,366, filed Sep. 20, 2011, entitled, "Conditional Electrical Stimulation," which is a continuation-in-part of International Application Serial No. PCT/US10/028406, filed Mar. 24, 2010, which claimed the benefit of U.S. Provisional Patent Application Ser. No. 61/164,222, filed Mar. 27, 2009. U.S. patent application Ser. No. 13/237,216 is also a continuation-in-part of International Application Serial No. PCT/US10/028400, filed Mar. 24, 2010, which claimed the benefit of U.S. Provisional Patent Application Ser. No. 61/164,225, filed Mar. 27, 2009. U.S. patent application Ser. No. 13/237,216 is also a continuation-in-part of International Application Serial No. PCT/US10/028396, filed Mar. 24, 2010, which claimed the benefit of U.S. Provisional Patent Application Ser. No. 61/164,232, filed Mar. 27, 2009. The entirety of each of these documents is incorporated herein by reference.

TECHNICAL FIELD

The disclosure relates to medical devices and, in particular, devices for the treatment of pelvic floor disorders.

BACKGROUND

Urinary incontinence, fecal incontinence, pelvic pain, sexual dysfunction and other pelvic floor disorders are common problems afflicting people of all ages, genders, and races. Various muscles, nerves, and organs within the pelvic floor cooperate to collect, store and release urine and fecal matter. Likewise, various pelvic muscles, nerve and organs support proper sexual function. A variety of disorders may compromise pelvic health, and contribute to incontinence, sexual dysfunction or pain. Many of the disorders may be associated with aging, injury or illness.

In some cases, incontinence can be attributed to improper sphincter function. For example, aging can often result in weakened sphincter muscles, which causes incontinence. Some patients may also suffer from nerve disorders that prevent proper triggering and operation of the bladder or sphincter muscles. Nerves running though the pelvic floor stimulate contractility in the sphincters. A breakdown in communication between the nervous system and the urinary or anal sphincter can result in incontinence or undesired retention.

Therapies for treating incontinence, pelvic pain, or sexual dysfunction include delivery of electrical stimulation. For example, delivery of electrical stimulation from an implantable medical device to nerves in the pelvic floor, such as the sacral and pudendal nerves, may provide an effective therapy for various pelvic floor disorders. As one example, electrical stimulation of the sacral nerve may modulate afferent nerve activities to restore urinary function. As another example, electrical stimulation of the nerves innervating pelvic floor muscles may strengthen pelvic floor muscle and promote urinary continence.

SUMMARY

In general, the disclosure describes techniques for providing conditional electrical stimulation to a patient to alleviate or manage pelvic floor disorders and promote pelvic health. An implantable medical device (IMD) may adjust a delivery cycle of electrical stimulation applied to a patient based on one or more of the following: a time in a time schedule, a control device output from a control device, and physiological information from a physiological information sensing device. As an example, the IMD may monitor a status of one or more inputs of the IMD and adjust the delivery cycle of the electrical stimulation applied to the patient based on the status of the input(s).

In one example, the disclosure provides a method comprising applying electrical stimulation from an electrical stimulation device to a patient, and adjusting a delivery cycle of the electrical stimulation in response to a time in a time schedule.

In another example, the disclosure provides another method comprising applying electrical stimulation from an electrical stimulation device to a patient, and adjusting a delivery cycle of the electrical stimulation in response to user input.

In an additional example, the disclosure provides another method comprising applying electrical stimulation from an electrical stimulation device to a patient, and adjusting a delivery cycle of the electrical stimulation in response to physiological information from a physiological information sensing device.

In another example, the disclosure provides an electrical stimulator comprising a therapy delivery circuit that delivers electrical stimulation therapy, and a processor that controls the therapy delivery circuit such that in response to a time in a time schedule, the processor adjusts a delivery cycle of the electrical stimulation.

In an additional example, the disclosure provides an electrical stimulator comprising a therapy delivery circuit that delivers electrical stimulation therapy, and a processor that controls the therapy delivery circuit to adjust a delivery cycle of the electrical stimulation based on user input.

In another example, the disclosure provides an electrical stimulator comprising a therapy delivery circuit that delivers electrical stimulation therapy, and a processor that controls the therapy delivery circuit to adjust a delivery cycle of the electrical stimulation in response to physiological information from a physiological information sensing device.

In yet another example, the disclosure provides a device comprising means for applying electrical stimulation from an electrical stimulation device to a patient, and means for adjusting a delivery cycle of the electrical stimulation in response to a time in a time schedule.

In still another example, the disclosure provides a device comprising means for applying electrical stimulation from an electrical stimulation device to a patient, and means for adjusting a delivery cycle of the electrical stimulation in response to user input.

In another example, the disclosure provides a device comprising means for applying electrical stimulation from an electrical stimulation device to a patient, and means for adjusting a delivery cycle of the electrical stimulation in response to physiological information from a physiological information sensing device.

The details of one or more examples are set forth in the accompanying drawings and the description below. Other features, objects, and advantages will be apparent from the description and drawings, and from the claims.

BRIEF DESCRIPTION OF THE DRAWINGS

FIGS. 9-11 depict electrical stimulation pulse trains having different delivery cycles.

DETAILED DESCRIPTION

Figure 1:
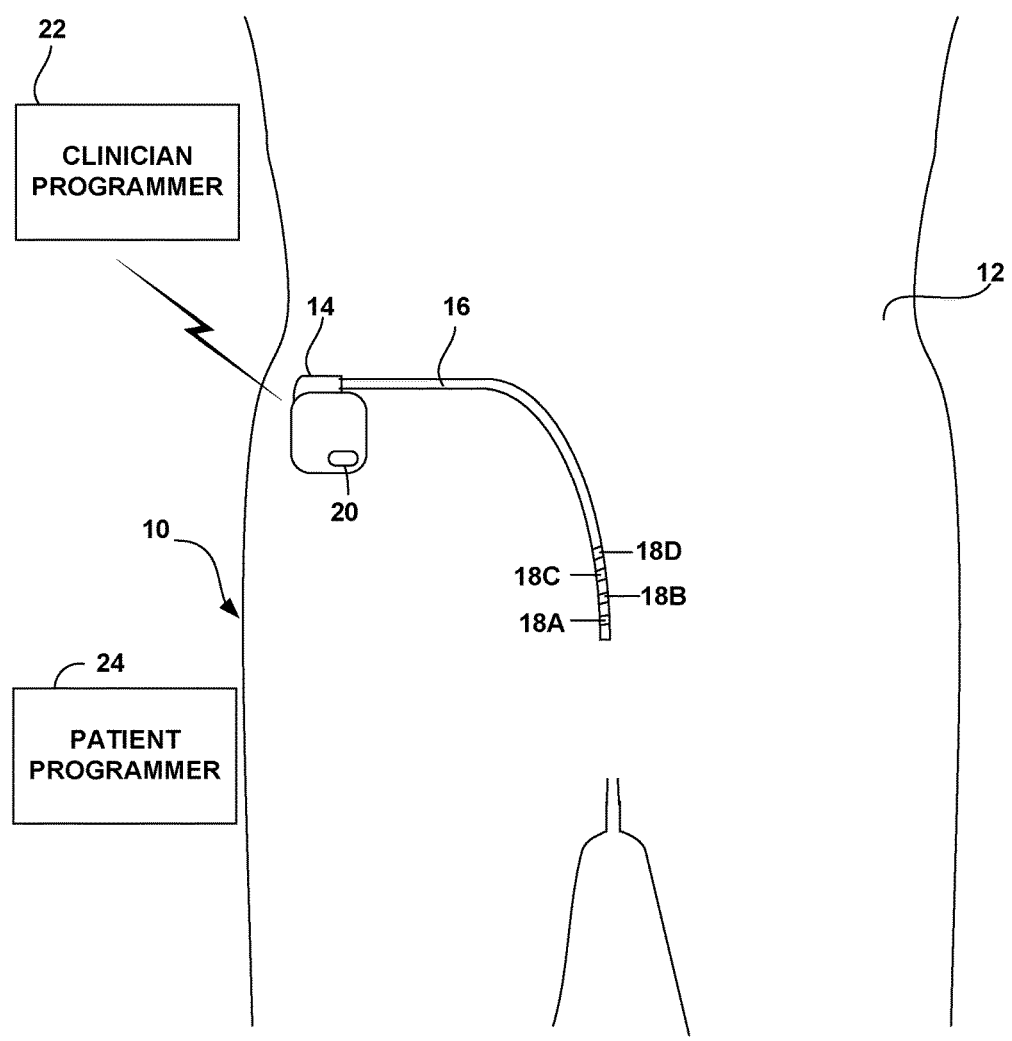
FIG. 1 is a schematic diagram illustrating a neurostimulation system providing neurostimulation therapy for incontinence.

In general, the disclosure describes techniques for providing conditional electrical stimulation to a patient to alleviate or manage pelvic floor disorders and promote pelvic health. An IMD may adjust a delivery cycle of electrical stimulation applied to a patient based on a time in a time schedule, a control device output from a control device, and/or physiological information from a physiological information sensing device. As an example, the IMD may monitor a status of one or more inputs of the IMD and adjust the delivery cycle of the electrical stimulation applied to the patient based on the status of the input(s). In various implementations, the IMD may monitor one of the inputs or a combination of the inputs as a basis for variation of the delivery cycle.

By adjusting the delivery cycle of electrical stimulation at least partially to provide conditional electrical stimulation, the overall amount of stimulation applied to the patient may be reduced, in comparison to continuous stimulation. With a reduced amount of stimulation, the patient may be less susceptible to undesirable side effects of electrical stimulation, such as nerve fatigue, accommodation, habituation or desensitization. In addition, delivery of conditional stimulation instead of continuous stimulation may reduce power consumption and thereby conserve power. Reduced power consumption may promote device longevity, reduce the frequency of device replacement surgery, permit reduction in power source size and overall IMD size, and extend the time between recharge cycles, if applicable.

A delivery cycle generally refers to the percentage of time that IMD 14 is delivering stimulation (e.g., stimulation pulses, stimulation pulse bursts, etc.) versus the percentage of time during which IMD 14 is not delivering stimulation. In some examples, the delivery cycle may be a pulse duty cycle and may refer to the percentage of time that IMD 14 is delivering a stimulation pulse versus the percentage of time during which IMD 14 is not delivering stimulation pulses between successive pulses. In this case, the delivery cycle may refer to an ON:OFF ratio that indicates the ratio of the time duration, e.g., a first time duration, of each pulse (an ON time) that is delivered versus the time duration, e.g., a second time duration, between successive pulses (an OFF time). In other examples, delivery cycle may be a pulse train duty cycle or a pulse burst duty cycle and may refer to the percentage of time that IMD 14 is delivering stimulation pulses versus the percentage of time during which IMD 14 is not delivering pulses between successive pulse trains, as shown and described in more detail below with respect to FIG. 8. In this case, the delivery cycle may refer to an ON:OFF ratio that indicates the ratio of a time duration, e.g., a first time duration, for which a pulse train comprising a series of pulses (i.e., a pulse burst) is delivered (an ON time) versus the time duration, e.g., a second time duration, between delivery of successive pulse bursts. Examples of adjusting delivery cycles are described in more detail below.

FIG. 1 is a schematic diagram illustrating an electrical stimulation system 10 that provides electrical stimulation therapy to control the function of pelvic floor nerves, pelvic floor muscles, or other pelvic floor anatomy in a patient 12. The electrical stimulation may be formulated to treat urinary or fecal incontinence, pelvic pain, sexual dysfunction, or other pelvic floor disorders, and thereby promote pelvic health. System 10 includes IMD 14, implantable medical lead 16, electrodes 18A-18D ("electrodes 18") disposed proximate to a distal end of leads 16, sensor 20, clinician programmer 22, and patient programmer 24. IMD 14 may be configured and implanted to deliver electrical stimulation to a pelvic floor nerve, a pelvic floor muscle, the urinary sphincter, the anal sphincter, or other pelvic floor targets, for instance.

IMD 14 provides a programmable electrical stimulation signal (e.g., in the form of electrical pulses) that is delivered to a target therapy site by implantable medical lead 16, and more particularly, via one or more stimulation electrodes 18 carried by lead 16. In the example of FIG. 1, IMD 14 includes lead 16. In other examples, IMD 14 may be a leadless stimulator, sometimes referred to as a microstimulator, or combination of such stimulators. In additional examples, IMD 14 may include two or more leads. The target therapy site may, for example, be the urinary sphincter, the anal sphincter, a pelvic floor muscle, or pelvic floor nerve. Pelvic floor nerves include peripheral nerves such as sacral nerves, pudendal nerves and associated branches, and dorsal genital nerves. In some examples, IMD 14 may be coupled to two or more leads, e.g., for bilateral or multilateral stimulation. A proximal end of lead 16 may be both electrically and mechanically coupled to IMD 14 either directly or indirectly (e.g., via a lead extension). Electrical conductors disposed within a lead body of lead 16 electrically connect stimulation electrodes 16 (and sense electrodes, if present) to a therapy delivery circuit within IMD 14.

System 10 may also include clinician programmer 22 and patient programmer 24. Clinician programmer 22 may be a handheld computing device that permits a clinician to communicate with IMD 14 during initial programming of IMD 14, and for collection of information and further programming during follow-up visits. Clinician programmer 22 supports wireless telemetry (e.g., proximal inductive telemetry, radio frequency (RF) telemetry or telemetry via the Medical Implant Communication Service (MICS)) with IMD 14 to download electrical stimulation parameters and therapy programs to the IMD and, optionally, upload operational data, patient activity data or other data stored, and sometimes collected, by IMD 14. In this manner, the clinician may periodically interrogate IMD 14 to evaluate efficacy of the stimulation therapy and, if necessary, modify the stimulation parameters.

Like clinician programmer 22, patient programmer 24 may be a handheld computing device. Patient programmer 24 may also include a user interface comprising input keys to allow patient 12 to interact with patient programmer 24 and IMD 14. In this manner, patient programmer 24 provides patient 12 with an interface to control electrical stimulation delivered by IMD 14. For example, patient 12 may use patient programmer 24 to start, stop or adjust electrical stimulation. In particular, patient programmer 24 may permit patient 12 to adjust stimulation parameters such as delivery cycle, duration, voltage or current amplitude, pulse width, and pulse rate, or select from stored programs comprising electrical stimulation therapy parameter sets. In one example, the stimulation parameters may be adjusted within an adjustment range specified by the clinician. Patient 12 may also retrieve information collected by IMD 14 via patient programmer 24. For example, patient programmer 24 may provide patient activity to patient 12 in the form of, for example, a statistic, a graphical representation, or a message relating to therapy efficacy.

Figure 2:
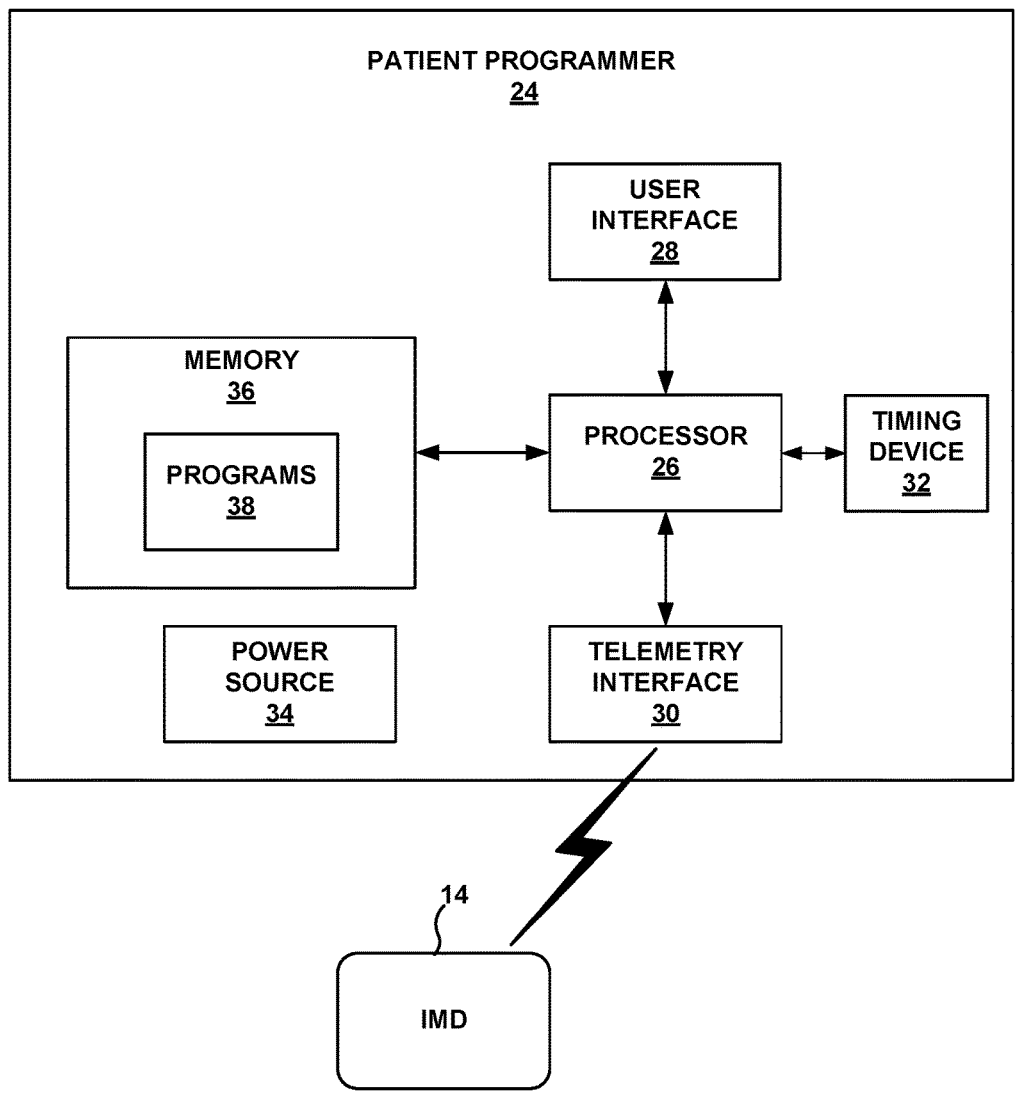
FIG. 2 is a block diagram illustrating an external monitor/programmer.

FIG. 2 is a block diagram illustrating example components of patient programmer 24 that receive patient input and communicate with stimulator 14. As shown in FIGS. 1 and 2, patient programmer is an external programmer that patient 12 may use to control the electrical stimulation delivered by IMD 14. Patient programmer 24 may include processor 26, user interface 28, telemetry interface 30, timing device 32, power source 34, and memory 36. Described in greater detail below and consistent with the techniques of this disclosure, memory 36 may include a number of programs 38 comprising electrical stimulation parameters. Each program 38 may specify the manner (e.g., delivery cycle, amplitude, width, or the like) in which electrical stimulation should be delivered to the patient 12 via IMD 14. Consistent with the techniques described in this disclosure and as will be described in more detail below, at least some of programs 38 may be based on one or more time schedules. A time schedule may, for example, be based on the time of the day, the day of the week, circadian rhythms, or the like. A clinician may use the clinician programmer (not shown) to download programs 38 and/or program groups into IMD 14 so that IMD 14 may locally execute the programs. Patient 12 may select one or more programs 38 or adjust one or more parameters associated with such programs (e.g., pulse width, pulse rate, amplitude, or the like) using patient programmer. Patient 12 may carry patient programmer 24 throughout therapy so that the patient can initiate, stop and/or adjust stimulation as needed.

While patient programmer 24 may be any type of computing device, the patient programmer may preferably be a hand-held device with a display and input mechanism associated with user interface 28 to allow interaction between patient 12 and patient programmer 24. Patient programmer 24 may be similar to a clinician programmer used by a clinician to program IMD 14. The clinician programmer may differ from the patient programmer by having additional features not offered to patient 12 for security, performance, or complexity reasons.

User interface 28 may include display and keypad (not shown), and may also include a touch screen or peripheral pointing devices. User interface 28 may be designed to receive an indication from patient 12 to deliver electrical stimulation. The indication may be in the form of a patient input such as pressing a button representing the start of therapy, or selecting an icon from a touch screen, for example. In alternative examples, user interface 28 may receive an audio cue from patient 12, e.g., the patient speaks into a microphone in order to perform functions such as beginning stimulation therapy. Patient programmer 24 acts as an intermediary for patient 12 to communicate with IMD 14 for the duration of therapy.

Processor 26 may include one or more processors such as a microprocessor, a controller, a digital signal processor (DSP), an application-specific integrated circuit (ASIC), a field programmable gate array (FPGA), discrete logic circuitry, or the like. Processor 26 may control user interface 28 to display information, and perform certain functions when requested by patient 12 via input to the user interface. Processor 26 may retrieve data from and/or store data in memory 36 in order to perform the functions of patient programmer 24 described in this disclosure.

As mentioned above, memory 36 may include programs 38 comprising electrical stimulation parameters. As such, programs 38 include data that defines the parameters of the electrical pulses delivered to patient 12. When a new program is requested by IMD 14 or patient 12, one of programs 38 may be retrieved from memory 36 and transmitted to IMD 14 in order adjust the electrical stimulation. Alternatively, patient 12 may generate a new program during therapy and store it with programs 38. Memory 36 may include any volatile, non-volatile, fixed, removable, magnetic, optical, or electrical media, such as a RAM, ROM, CD-ROM, hard disk, removable magnetic disk, memory cards or sticks, NVRAM, EEPROM, flash memory, and the like.

While patient programmer 24 may generally be described as a hand-held computing device, the patient programmer may be a notebook computer, a cell phone, or a workstation, for example. In some embodiments, patient programmer 24 may comprise two or more separate devices that perform the functions ascribed to the patient programmer. For example, patient 12 may carry a key fob that is only used to start or stop electrical stimulation. The key fob may then be connected to a larger computing device having a screen via a wired or wireless connection when information between the two needs to be synchronized.

Although a separate figure directed to clinician programmer 22 has not been provided in this disclosure, in some examples clinician programmer 22 may be similar to patient programmer 24 but provide more full function programming capabilities.

Figure 3:
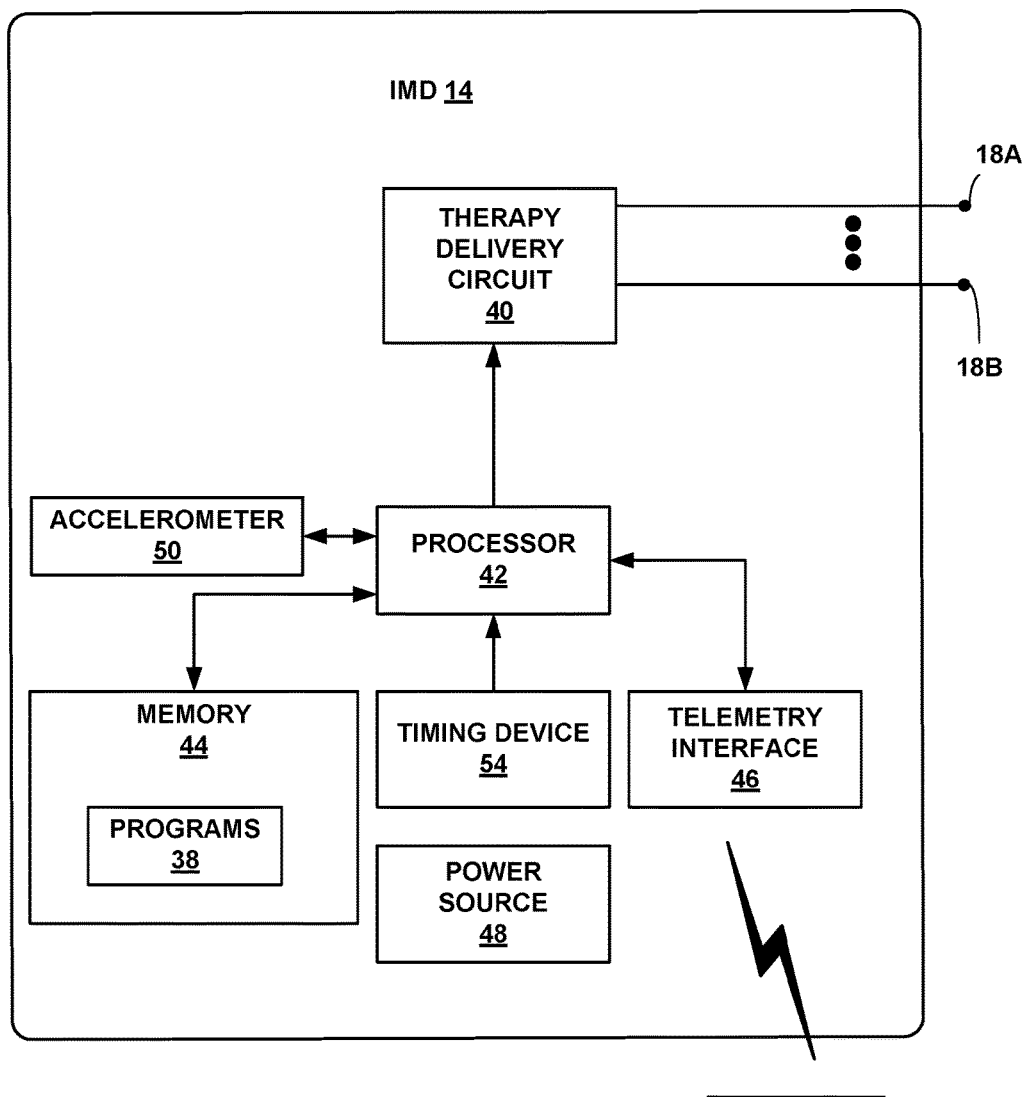
FIG. 3 is a block diagram illustrating an implantable neurostimulator.

FIG. 3 is a block diagram illustrating example components of IMD 14 that deliver electrical stimulation to patient 12. In the example of FIG. 3, IMD 14 includes therapy delivery circuit 40, processor 42, memory 44 including a number of therapy programs 38, wireless telemetry interface 46, and power source 48. Processor 42 may receive input signals from control device 52. Control device 52 may be, for example, an external control device such as patient programmer 24. Or, in another example, control device 52 may be part of IMD 14 itself, thereby allowing a patient to "tap" his or her finger over or superior the position in which IMD 14 is implanted in order to trigger the device. Or, in another example, control device 52 may be a device implanted within a subcutaneous tissue, thereby allowing the patient to "tap" his or her finger above or superior to the device in order to trigger the device. Such a device is described in detail in U.S. Patent Application Publication No. 2008/0300651. In some examples, IMD 14 may generally conform to the Medtronic Interstim Neurostimulator, manufactured and marketed by Medtronic, Inc., of Minneapolis, Minn. However, the structure, design, and functionality of IMD 14 may be subject to wide variation without departing from the scope of the disclosure as broadly embodied and described.

Processor 42 controls therapy delivery circuit 40 by setting and adjusting stimulation parameters such as delivery cycle, voltage or current amplitude, pulse rate, and pulse width. In some examples, therapy delivery circuit 40 delivers pulsed stimulation. In other examples, therapy delivery circuit 40 delivers stimulation in the form of continuous waveforms. Processor 42 may be responsive to parameter adjustments or parameter sets received from patient programmer 24 via telemetry interface 46. Hence, patient programmer 24 may program IMD 14 with different sets of operating parameters.

Memory 44 stores instructions for execution by processor 42, including operational commands and programmable parameter settings. Example storage areas of memory 44 may include instructions associated with programs 38. Programs 38 may include each program used by IMD 14 to define parameters and electrode combinations for delivering electrical stimulation to patient 12. In one example, programs 38 may include parameters for delivering electrical stimulation associated with a time schedule. Processor 38 may access a clock or other timing device 54 within IMD 14 to determine appropriate times to apply programs 38 based on the time schedules associated with programs 38. In another example, programs 38 may include parameters for delivering electrical stimulation in response to processor 42 receiving a control device output from control device 52. In another example, programs 38 may include parameters for delivering electrical stimulation in response to processor 42 receiving physiological information from a physiological information sensing device, e.g., such as accelerometer 50.

Memory 44 may include one or more memory modules constructed, e.g., as random access memory (RAM), read-only memory (ROM), non-volatile random access memory (NVRAM), electrically erasable programmable read-only memory (EEPROM), and/or FLASH memory. Processor 42 may access memory 44 to retrieve instructions for control of therapy delivery circuit 40 and telemetry interface 46, and may store information in memory 44, such as operational information.

Wireless telemetry in IMD 14 may be accomplished by radio frequency (RF) communication, MICS, or proximal inductive interaction of IMD 14 with patient programmer 24 via telemetry interface 46. Processor 42 controls telemetry interface 46 to exchange information with patient programmer 24. Processor 42 may transmit operational information and receive electrical stimulation parameter adjustments or parameter sets via telemetry interface 26. Also, in some examples, IMD 14 may communicate with other implanted devices, such as stimulators, control devices, or sensors, via telemetry interface 46.

Power source 48 delivers operating power to the components of IMD 14. Power source 48 may include a battery and a power generation circuit to produce the operating power. In some examples, the battery may be rechargeable to allow extended operation. Recharging may be accomplished through proximal inductive interaction between an external charger and an inductive charging coil within IMD 14. In other examples, an external inductive power supply may transcutaneously power IMD 14 whenever stimulation therapy is to occur.

IMD 14 is coupled to electrodes 18, which may correspond to electrodes 18 illustrated in FIG. 1, via one or more leads 16. IMD 14 provides electrical stimulation to a target therapy site such as a pelvic floor muscle or pelvic floor nerve of patient 12. IMD 14 includes suitable signal generation circuitry for generating a voltage or current waveform with a selected delivery cycle, amplitude, pulse width, and pulse rate. In general, as described in this disclosure, the electrical pulses generated by therapy delivery circuit 40 may be generated with delivery cycles, pulse widths, and pulse amplitudes for appropriate times suitable to reduce pelvic pain, or prevent urinary or fecal incontinence, or alleviate sexual dysfunction, without excessive consumption of power provided by power source 48. Therapy delivery circuit 40 may include voltage or current sources known in the art for generating stimulation. An exemplary range of neurostimulation stimulation pulse parameters likely to be effective in treating incontinence, pelvic pain or sexual dysfunction, e.g., when applied to the sacral or pudendal nerves of a human patient, are as follows:

1. Frequency: between approximately 0.5 Hz and 100 Hz, more preferably between approximately 3 Hz and 60 Hz, and still more preferably between approximately 5 Hz and 40 Hz.

2. Voltage Amplitude: between approximately 0.1 volts and 50 volts, more preferably between approximately 0.5 volts and 20 volts, and still more preferably between approximately 1 volt and 10 volts.

3. Pulse Width: between about 10 microseconds and 5000 microseconds, more preferably between approximately 100 microseconds and 1000 microseconds, and still more preferably between approximately 180 microseconds and 450 microseconds.

Figure 4:
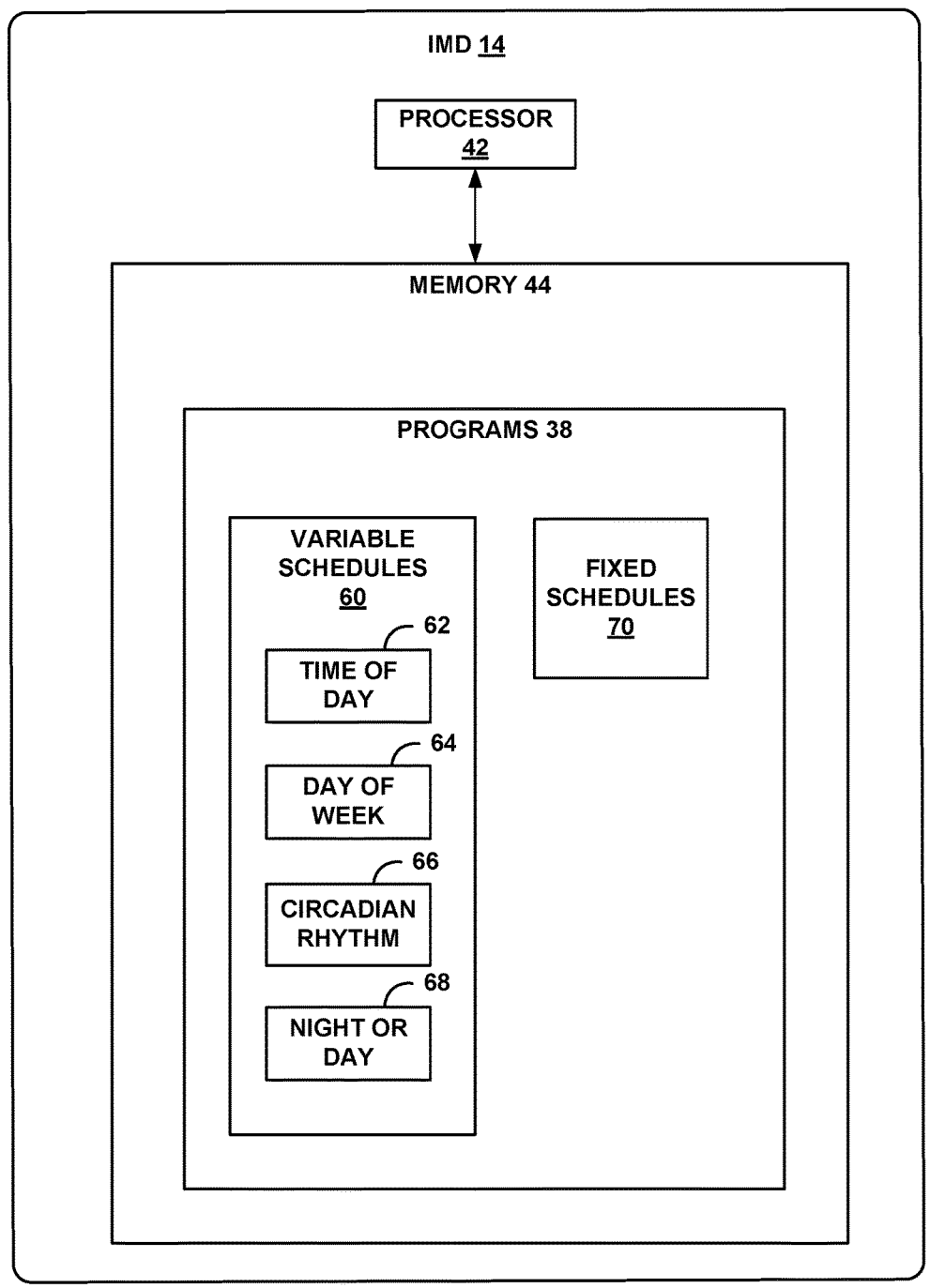
FIG. 4 is a block diagram illustrating a memory of an implantable neurostimulator storing different time schedules.

FIG. 4 is a block diagram illustrating memory 44 of IMD 14 storing programs 38 that may be executed by processor 42 of IMD 14 to deliver electrical stimulation to patient 12. As shown and described above with respect to FIG. 3, processor 42 may receive an input from timing device 54 and select one of programs 38 based on the current time and the time schedule associated with program 38. After consulting with patient 12 to ascertain the daily routine, work schedule, sleep schedule, lifestyle, or the like of patient 12, a clinician may prescribe one or more programs 38 based on a time schedule. The clinician may initially download programs 38 into memory 36 of patient programmer 24 as well as memory 44 of IMD 14. Thus, IMD 14 may deliver patient-specific conditional stimulation to patient 12 via IMD 14, where, in this example, the condition is a time schedule.

In one example, program 38 may be executed based on the time of the day. Patient 12 may have informed the clinician that patient 12 typically goes to bed at 10 pm, wakes up at 6 am, eats breakfast immediately with a cup of coffee, and arrives at work by 7 am. The patient may not have a break at work until 9 am. Based on this morning routine, the clinician may prescribe parameters of program 38 that, when executed by processor 42, provides electrical stimulation having a first delivery cycle "A" during the period in which the patient is sleeping. Then, at 6 am, processor 42, in response to receiving an input from timing device 54, executes another instruction of program 38 in the manner defined by the time schedule associated with program 38. That is, program 38 defines times at which processor 42 will apply specific delivery cycle parameters associated with those times to therapy deliver circuit 40. So, at 6 am, processor 42 modifies the electrical stimulation applied by therapy deliver circuit 40 to produce a stimulation having a second delivery cycle "B." In this manner, the delivery cycle of the electrical stimulation is varied in response to receiving a delivery cycle parameter associated with a time in a time schedule.

As mentioned previously, delivery cycle generally refers to the percentage of time that IMD 14 is delivering stimulation pulses versus the percentage of time during which IMD 14 is not delivering pulses. In some examples, delivery cycle may refer to the percentage of time that IMD 14 is delivering stimulation pulses versus the percentage of time during which IMD 14 is not delivering pulses between successive pulses. In other examples, delivery cycle may refer to the percentage of time that IMD 14 is delivering stimulation pulses versus the percentage of time during which IMD 14 is not delivering pulses between successive pulse trains. Examples of adjusting delivery cycles are described in more detail below.

Adjusting the delivery cycle may reduce the power consumption of IMD 14. If the percentage of time that IMD 14 is not delivering pulses is increased, the amount of power consumed by IMD 14 will decrease. Further, adjusting the delivery cycle may result in less stimulation of the nerve. Less stimulation of the nerve may result in reducing the potential side effects of chronic continuous stimulation, such as nerve accommodation, or habituation. Nerve accommodation, or habituation, refers to a condition of the nerve in which, after continuous stimulation over a period of time, the nerve may require increasing levels of stimulation (e.g., increased amplitude, pulse width, pulse rate, or the like) to be delivered in order to achieve the same level of reaction. And, adjusting the delivery cycle may reduce the intensity of the stimulation required by leveraging any carry-over, or residual, effect. The term "carry-over effect" generally refers to the effect of stimulation continuing on to some degree past the time that stimulation ended. This carry-over effect is the reason that a continuous train of pulses may not be needed in order to provide adequate stimulation to a patient. The carry-over effect causes the nerve, muscle, or other area of stimulation to retain the effects of stimulation beyond the time that stimulation was applied. Carry-over effect is described in more detail below.

A greater delivery cycle delivers more stimulation to a target area, which may be desirable and/or necessary at certain times or for certain activities. However, it may be desirable to reduce the delivery cycle at other times. In between pulses or pulse trains, the stimulation effect may decay to a certain level, and the level to which the stimulation effect is allowed to decay is a function of the delivery cycle. Less decay may be desirable for times or activities where incontinence may be more likely. As such, it may be desirable to increase the delivery cycle and, in turn, reduce the time between successive pulses or pulse trains, thereby limiting the decay of the stimulation effect.

In the above example, it may be desirable for delivery cycle "B" to be greater than that of delivery cycle "A." If delivery cycle "B" was greater than that of delivery cycle "A," then the percentage of time that IMD 14 delivers stimulation pulses to the patient would be greater during delivery cycle "B" then during delivery cycle "A." Providing more stimulation to the patient during the morning between 6 am and 9 am while the patient is at work and unable to take a break may reduce the possibility of an incontinence event because of the leveraging of the carry-over effect.

Continuing the example from above, the patient may have also informed the clinician that the patient's break is usually over at 9:15 am and another break is not usually expected until 12 noon. Based on this information, the clinician may have included in program 38 instructions to be executed by processor 42 at 9:15 am. Processor 42, in response to receiving an input from timing device 54 indicating time of day, executes the instructions and applies the delivery cycle parameter(s) stored in memory 44 associated with 9:15 am. Thus, therapy delivery circuit 40 applies an electrical pulse having a third delivery cycle "C." It may be desirable for delivery cycle "C" to be less than that of delivery cycle "B." If delivery cycle "C" was less than that of delivery cycle "B," then the percentage of time that IMD 14 delivers stimulation pulses to the patient would be less during delivery cycle "C" than during delivery cycle "B." Given that the patient most likely voided during the break, providing less stimulation may be desirable, as more intensive stimulation may not be immediately necessary following a urinary voiding break. In the manner described above, the clinician may develop a program that is patient-specific based on the patient's daily schedule.

In another example, program 38 may be executed based on the day of week. Continuing the example started above, the patient may have informed the clinician that the patient's work schedule is Monday through Friday. As such, the constraints placed on the patient regarding when breaks may be taken during Monday through Friday are not necessarily applicable on Saturday and Sunday. Rather, the patient may generally be home during Saturday and Sunday mornings, for example. And, the patient may wake up at 7 am during the weekends. Based on this information, the clinician may prescribe another program 38 for weekends that may be different from the program 38 prescribed for weekdays. For example, the clinician may prescribe a program that has a delivery cycle "A" during the period in which the patient is sleeping, and then at 7 am, processor 42, in response to receiving an input from timing device 54, executes the instructions and applies the delivery cycle parameter(s) stored in memory 44 associated with 7 am. Thus, therapy delivery circuit 40 applies an electrical stimulation pattern having a delivery cycle "D." In the above example, it may be desirable for delivery cycle "D" to be less than that of delivery cycle "A." That is, the percentage of time that IMD 14 would be delivering stimulation pulses to the patient would be greater during delivery cycle "A" (i.e., during the time the patient is sleeping) then during delivery cycle "D." In contrast to the weekday mornings, the patient does not need to have as much electrical stimulation during the weekend mornings because the patient is able to take a break when needed. The clinician may further develop the weekend program in consultation with the patient to take account of the patient's habits and behavior during the weekend days and nights.

It should noted that adjusting the delivery cycle is different from simply turning the stimulation on and off at certain times of the day or certain days of the week. As mentioned above, delivery cycle generally refers to the percentage of time that IMD 14 is delivering stimulation pulses versus the percentage of time during which IMD 14 is not delivering pulses. Adjusting the delivery cycle thus refers to adjusting the percentage of time that IMD 14 is delivering or not delivering stimulation pulses. Simply turning the stimulation on or off does not adjust the delivery cycle.

The patient may also participate in certain scheduled activities outside of work around which an electrical stimulation program may be tailored. For example, the patient may participate in an organized physical activity every Tuesday and Saturday night at 7 pm. Based on this information, the clinician can adjust the weekday and weekend programs to include a program such that at 7 pm, processor 42, in response to receiving an input from timing device 54, executes an instruction of program 38 in the manner defined by the time schedule associated with program 38. Thus, therapy delivery circuit 40 applies an electrical stimulation pattern having a delivery cycle defined by the delivery cycle parameters associated with 7 pm on Tuesday or Saturday in program 38. The electrical stimulation applied by therapy delivery circuit 40 at 7 pm on a Tuesday or Saturday may have a relatively high delivery cycle as compared to the delivery cycles that are used at other times of the day. This relatively high delivery cycle may be provided in order to counteract the stress placed on the pelvic floor region, including the pelvic floor muscles, that may result from increased activity. Without a higher delivery cycle, the patient may be more likely to have an incontinence event during the period of increased physical activity. Later, at a defined point in time after the period of activity, program 38 may reduce the delivery cycle.

In some examples, a low delivery cycle may be in the range of approximately 10% ON and 90% OFF to approximately 30% ON and 70% OFF. In other examples, a low delivery cycle may be in the range of approximately 20% ON and 80% OFF to approximately 25% ON and 75% OFF. In one specific example, a low delivery cycle may be approximately 10 seconds ON and 50 seconds OFF, or approximately 16.7% ON and 83.3% OFF.

In some examples, a medium delivery cycle may be in the range of approximately 30% ON and 70% OFF to approximately 70% ON and 30% OFF. In other examples, a medium delivery cycle may be in the range of approximately 40% ON and 60% OFF to approximately 50% ON and 50% OFF. In one specific example, a medium delivery cycle may be approximately 16 seconds ON and 8 seconds OFF.

In some examples, a high delivery cycle may be in the range of approximately 70% ON and 30% OFF to approximately 100% ON. In other examples, a high delivery cycle may be in the range of approximately 80% ON and 20% OFF to approximately 90% ON and 10% OFF. The low, medium, high delivery cycle may be used at low, medium, and high bladder capacity, respectively.

Additional programs based on time schedules may be based on day versus night. That is, a patient, such as the patient in the example above, may generally be awake during the day and asleep at night. As such, it may be desirable to provide the patient with a nighttime program having a specific delivery cycle in order to prevent incontinence events while sleeping. Such a program may provide for an electrical stimulation pattern that has a delivery cycle that gradually increases throughout the night. It may be desirable to gradually increase the delivery cycle of electrical stimulation over the course of the night because, although the patient may have voided before going to sleep, he may also have ingested fluid or food immediately or shortly prior to going to sleep. The gradual increase in the delivery cycle over the course of the night thus takes into account the initial voiding event by providing less stimulation early in the night. The gradual increase in the delivery cycle over the course of the night also takes into account the possible ingestion of fluids or food prior to sleeping by providing more stimulation throughout the night as the patient approaches a time at which incontinence becomes more likely due to processing of fluids and food into urine and waste.

Additional programs based on time schedules may be based on circadian rhythms. A circadian rhythm generally refers to the daily pattern of an individual, based on a 24-hour interval. For example, a patient may be a shift worker, and in general, work at night and sleep during the day. As such, in one example, the patient may develop their own program via the patient programmer by manually inputting times of the day when the delivery cycle of the electrical stimulation should be increased, when the delivery cycle should be decreased, and the specific delivery cycles. In such a manner, these "learned" time schedules, via manual input by the patient, may be the result of the circadian rhythms of the patient.

In another example of circadian rhythm, rather than have the clinician program a time to increase the delivery cycle of the electrical stimulation for an activity that the patient may participate in, the patient may instead create a program using the patient programmer to include electrical stimulation for that activity at a specified time. For example, the patient may participate in physical activity on Tuesday and Saturday nights, but only for four months of the year. Instead of the clinician creating a weekly program, without an endpoint, to include electrical stimulation for an activity that only lasts for four months, the patient may instead create the program by manually inputting the days and times at which the patient requires electrical stimulation with an increased delivery cycle. In response, IMD 14 has "learned" a circadian rhythm of the patient, via manual input by the patient, and IMD 14 may then provide the electrical stimulation accordingly at specific times on Tuesday and Saturday nights until the patient modifies the program.

In an additional example of circadian rhythm, the program used by IMD 14 may be created using "adaptive learning" rather than manual entry by the patient. Continuing the example started above, if the patient is physically active on Tuesday and Saturday nights, rather than manually entering the days and times at which an electrical stimulation having an increased delivery cycle would be desired, IMD 14 may learn over time from the input of one or more sensors, such as accelerometers, that the patient is physically active regularly at specific times of the day on specific days of the week. IMD 14 may then create a program, or modify an existing program, that increases the delivery cycle of the electrical stimulation in response to the regular activity that it has "learned" from the sensor(s). IMD 14, and in particular, processor 42, may monitor one or more sensors, such as an accelerometer. When increased activity is detected, the date and time may be recorded in memory 44. For each period of increased activity detected, processor 42 may analyze the days and times in order to determine a pattern. If a pattern is detected, processor 42 may communicate the pattern to the patient programmer via telemetry interface 46. Patient programmer 24 may prompt the patient as to whether it would be desirable to add a new program with new delivery cycle parameters for that day and time.

The examples described above with respect to time schedules are variable cycling schedules. The time schedules are variable cycling schedules 60 because programs 38 vary according to the time of the day 62, the day of the week 64, circadian rhythms 66, night or day 68, asleep or awake status, or the like. In some examples, the techniques of this disclosure may be directed to fixed cycling schedules 70. While some patients may prefer a variable cycling schedule, other patients may prefer a fixed cycling schedule. In contrast to a variable cycling schedule, a fixed cycling schedule may provide a repeatable pattern of stimulation to the patient. The patient may desire to structure their daily schedule around the electrical stimulation provided by the IMD 14 rather than provide electrical stimulation based on their daily schedule. Using fixed cycling schedule 70, the patient may desire to have a relative high delivery cycle, and thus a relatively high stimulation effect or intensity, at specific times during the day, regardless of the day of the week. For example, the clinician may prescribe a program that provides electrical stimulation having a first delivery cycle from 6 am to 8 am, and at 8 am, processor 42, in response to receiving an input from timing device 54, executes an instruction of program 38 that applies a second delivery cycle to therapy delivery circuit 40. Therapy delivery circuit then delivers a stimulation having a second delivery cycle from 8am to 9 am, the second delivery cycle being greater than the first. Program 38 may include instructions that cause processor 42 to modify the electrical stimulation to produce an electrical pulse with the first delivery cycle from 9 am to 12 noon, at which time program 38 may again increase the delivery cycle of the stimulation to the second delivery cycle. Continuing in this manner, fixed cycling schedule 70 may be developed for the patient such that, regardless of the day of the week, the cycling schedule will remain the same throughout the day. The patient may then adjust his/her behavior and habits around the certainty provided by fixed cycling schedule 70.

Based on the above techniques of adjusting the delivery cycle of the applied electrical stimulation at least partially in response to a time schedule, the overall amount of stimulation applied to the patient and/or the time for which stimulation is applied to a patient, and particularly a nerve of the patient, may be minimized. For example, because the delivery cycle of the electrical stimulation is reduced after certain times of the day, or on certain days of the week, the nerve receives less stimulation. Less stimulation of the nerve may result in reducing the potential side effects of chronic continuous stimulation, such as nerve accommodation, or habituation. As mentioned above, nerve accommodation, or habituation, refers to a condition of the nerve in which, after continuous stimulation over a period of time, the nerve may require increasing levels of stimulation (e.g., increased amplitude, pulse width, pulse rate, or the like) to be delivered in order to achieve the same level of reaction. And, because less stimulation is needed, the techniques described above increase the longevity of the device, and in particular battery longevity, by reducing the power consumption. The increased device longevity may reduce the frequency of surgery for device replacement. Finally, by reducing the power consumption, a smaller power source such as a battery may be sufficient for the power requirements of the IMD, thereby permitting possible reduction in the overall size of the IMD 14.

It should be noted that control of the electrical stimulation may come from within IMD 14 or from an external programmer such as patient programmer 24, or from a combination of the two. If an external programmer such as patient programmer 24 controls the electrical stimulation, the external programmer may use its own clock, track the time schedules, and then transmit to IMD 14 via telemetry interface 30 program commands for adjusting the delivery cycle. Or, external programmer may transmit a time of day signal or schedule status signal, indicating that IMD 14 should execute locally stored program. In such a manner, control over the electrical stimulation may be distributed between IMD 14 and an external programmer, or may reside in either one alone.

Figure 5:
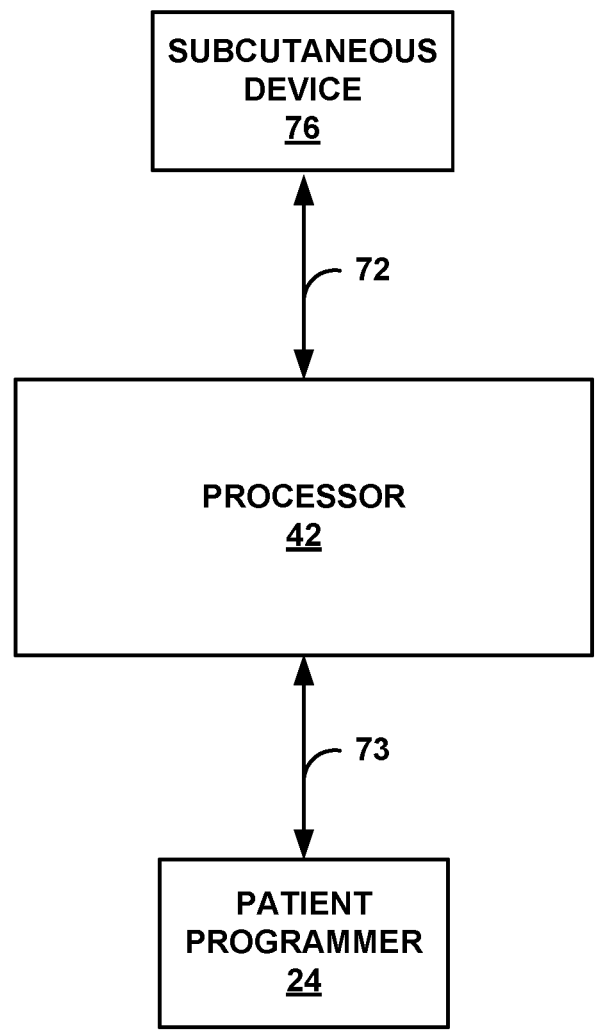
FIG. 5 is a block diagram illustrating a processor of an implantable neurostimulator receiving the control device output of a control device.

FIG. 5 is a block diagram illustrating processor 42 of IMD 14 receiving control device outputs 72, 73 from control devices like subcutaneous device 76 and patient programmer 24, respectively, for example. In response to receiving a signal associated with one or more control device outputs 72 from one or more control devices 52, processor 42 adjusts the delivery cycle of the electrical stimulation delivered by therapy delivery circuit 40. For example, processor 42 may adjust the delivery cycle of the electrical stimulation by increasing the delivery cycle to a defined level. In some examples, after increasing the delivery cycle to a defined level, processor 42 may gradually decrease the delivery cycle of the electrical stimulation over time. Thus, IMD 14 may deliver conditional stimulation to the patient 12 via IMD 14, where, in this example, the condition is a command entered by a user, e.g., via a control device such as patient programmer 24 or subcutaneous control device 76.

In one example, control device 52 may be an external device such as patient programmer 24. Processor 42 may receive a control device input from patient programmer 24 via telemetry interface 46. Processor 42 controls the delivery cycle of the electrical stimulation supplied to the patient via the therapy delivery circuit. In response to receiving the input from patient programmer 24, processor 42 adjusts the delivery cycle of the electrical stimulation provided to the patient. Processor 42 may adjust the delivery cycle of the stimulation by accessing parameters or programs 38 stored in memory 44 of IMD 14, for example. So, a patient may decide to use patient programmer 24 to increase the delivery cycle of the electrical stimulation provided by IMD 14 in order to prevent an incontinence event. In some examples, the patient may simply request a "boost" of the delivery cycle by some unspecified level, similar to a volume control. In other examples, the patient may increase the delivery cycle by a specified level (e.g., increase by 25%). In response to receiving control device output 72, processor 42 may increase the delivery cycle of the electrical stimulation using the programs or parameters pre-programmed into memory 44, thereby providing more stimulation to the patient. Memory 44 may store numerous different programs. Examples of specific programs may include a "sleeping mode," a "meeting mode," and a "jogging mode," each tailored to the patient's needs. For example, the stimulation provided by the "sleeping mode" may have a lower delivery cycle than that of the stimulation provided in the "meeting mode." However, the "jogging mode" may have a delivery cycle that is higher than the delivery cycle of the "meeting mode" based on the need for more stimulation during increased levels of physical activity. In such a manner, the control device output may be in response to a manual patient input entered based upon the patient's activity level (i.e., sleeping, jogging, etc.) or an activity type of the patient (i.e., meeting versus jogging, etc.) In some examples, the manual patient input may be the patient requesting a general "boost" of the delivery cycle by some unspecified level, as mentioned above. In other examples, the manual patient input may be the patient selecting a "jogging mode," a "meeting mode," a "sleeping mode," or the like.

As mentioned above, IMD 14 may alternatively or additionally provide electrical stimulation in order to reduce pelvic pain. The patient may use control device 52 in order to increase the electrical stimulation when a period of increased pelvic pain occurs. In such a manner, control device output 72 may be in response to a manual patient input entered in response to a level of pelvic pain.

Distinct control device outputs 72 may be provided based upon the patient's manual operation of control device 52, for example. By way of example, the patient may increase the level of delivery cycle by "tapping" once on subcutaneous device 76, and the patient may reduce the level of delivery cycle by "tapping" twice on subcutaneous device 76. The patient may also increase or decrease the level of delivery cycle using patient programmer 24. In this manner, processor 42 adjusts the delivery cycle of the electrical stimulation pulse in response to receiving a control device output from a control device. Additionally, processor 42 turns off stimulation for a certain period of time after receiving a control device output from a control device, then automatically resumes after a certain period of time, gradually increasing the delivery cycle of the electrical stimulation pulse. Turning off stimulation for a certain period of time may be desirable after a voiding event, for example, because a patient no longer immediately needs stimulation. Then, a gradual increase in delivery cycle over time after a voiding event may be desirable to automatically account for the increased stimulation needs of the patient as the patient's bladder fills, for example. In one example, the control device output from control device 52 may be the result of patient "tapping" the skin after a voiding event. In that case, the patient may want to turn off stimulation after the voiding event, but gradually allow it to increase over time automatically.

In response to a voiding event or defecation, the patient may use control device 52 to reduce the level of stimulation. After receiving control device output 72 indicative of a request for reduction in stimulation level from the patient, the processor 42 decreases the delivery cycle of the electrical stimulation based on programs 38 in memory 44, thereby providing less stimulation to the patient, as requested by the patient, in response to the voiding event. In one example, the electrical stimulation may automatically (i.e., without manual user intervention) and gradually increase over time after receiving a control device output following a voiding event. Hence, IMD 14 may provide less stimulation by reducing the delivery cycle immediately following the recent voiding event, but gradually increase stimulation by increasing the delivery cycle over time to account for the filling of the bladder. In another example, the electrical stimulation may automatically and gradually decrease over time after receiving a control device output indicative of a request for reduction in stimulation level from the patient following a voiding event.

As mentioned above, the patient may also increase the level of stimulation by manually indicating an increase using control device 52. Such a "boost" of delivery cycle may be temporary and extend for a period of minutes or hours. In some examples, the "boost" of delivery cycle may be turned off such that the stimulation returns to a baseline delivery cycle level immediately upon expiration of a timer. In other examples, the "boost" of delivery cycle may be gradually reduced over time such that the stimulation returns to a baseline delivery cycle level following a reduction profile.

In some examples, the "boost" of delivery cycle may last for a finite duration of time (e.g., ten minutes, twenty minutes, one hour, etc.) If the patient determines that the increased stimulation achieved through the "boost" of delivery cycle should be continued, then after expiration of the finite duration, or before the expiration of the finite duration, the patient may "reactivate" the "boost" of delivery cycle such that any reduction in stimulation is delayed. The expiration of finite duration, or the approaching of the expiration of the finite duration may be communicated to the patient by tactile, audible, text, or visual means via patient programmer 24, or by tactile means from IMD 14, for example. In other examples, the "boost" in delivery cycle may last indefinitely, leaving the patient in control of reducing the delivery cycle.

Figure 6:
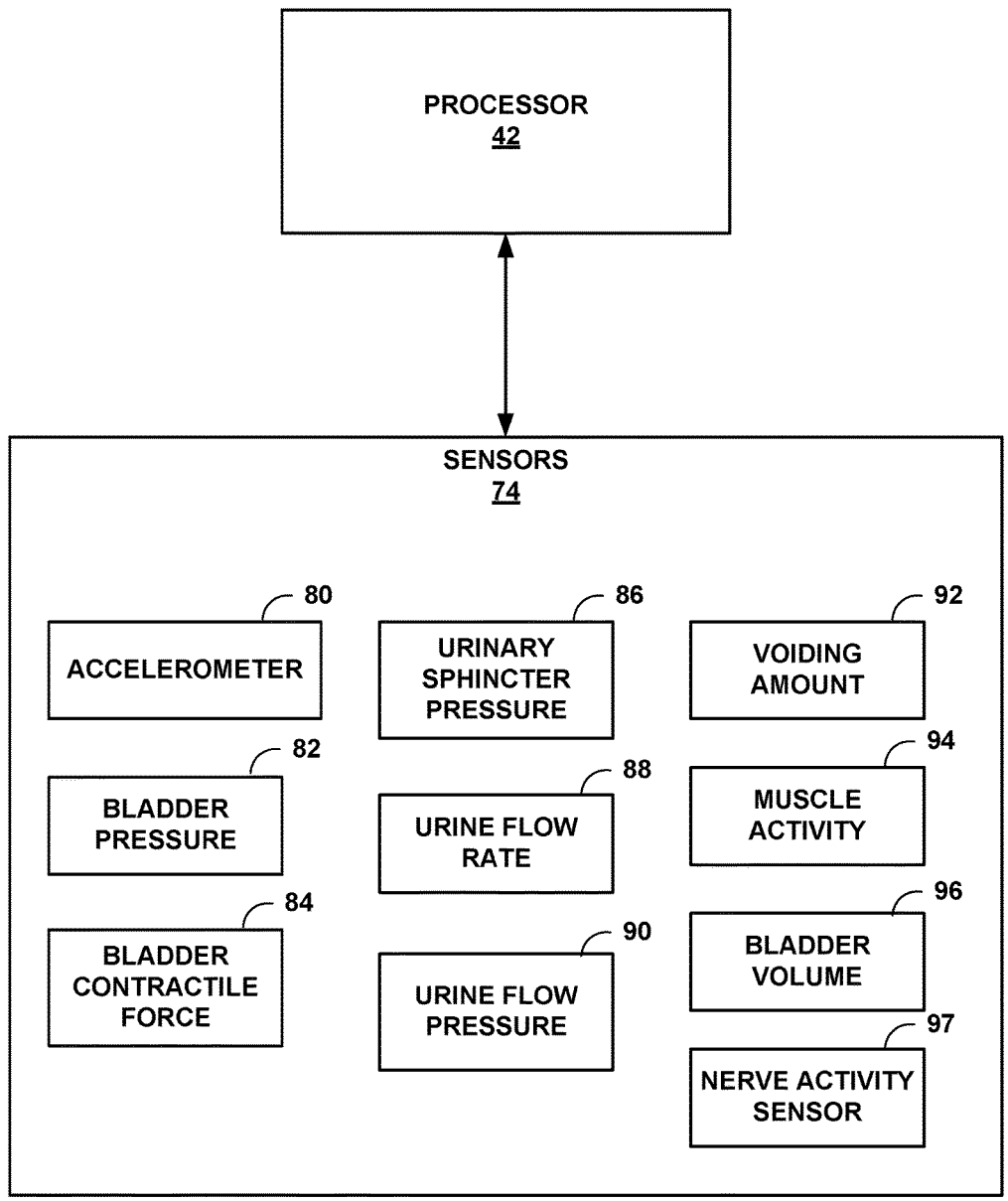
FIG. 6 is a block diagram illustrating a processor of an implantable neurostimulator receiving an input from one or more sensors.

Additionally, the patient may also use control device 52 to produce control device output 72 in response to receiving bio-feedback from a physiological information sensing device ("sensors") 74, such as those shown in FIG. 6. For example, the patient may receive bio-feedback indicating the volume of his bladder from a sensor. Bladder volume may be detected using sensors 74 implanted in or adjacent to the bladder, for example. Sensors 74 may transmit a signal to the patient indicating a fill level of the bladder. The signal may be communicated to the patient by tactile, audible, text, or visual means via patient programmer 24, or by tactile means from IMD 14, for example. In response to the bio-feedback from sensor 74, the patient may use control devices 52 such as patient programmer 24 or subcutaneous device 76 to produce control device output 72. Processor 42 receives control device output 72 and adjusts the delivery cycle of the electrical stimulation in response. Physiological information that may be measured and used as bio-feedback, includes, but is not limited to, bladder pressure, bladder contractile force, urinary sphincter pressure, urine flow rate, urine flow pressure, or voiding amount. Physiological information may be communicated to the patient by tactile, audible, text, or visual means via patient programmer 24, or by tactile means from IMD 14, for example.

As mentioned above, control device 52 may be a subcutaneous device 76. Subcutaneous device 76 is a device implanted within a subcutaneous tissue, for example. In some examples, subcutaneous device may be IMD 14 itself. Such a device generates a signal in response to a user defined input, such as the "tapping" of a finger on the skin above or superior to the device in order to trigger the device. The tapping of a finger on the skin refers to the motion of the patient pressing a finger downward into the skin located above or superior to the device and subsequently releasing the finger from the skin. Tapping the skin in this manner causes the epidermis and subcutaneous tissue, for example, to compress and/or deflect in the direction of motion. As described in detail in U.S. Patent Application Publication No. 2008/0300651, the mechanism of the device that generates the electrical signal based on the patient input may, for example, be a multiple or single axis accelerometer or a strain gauge that produces a detectable change in electrical resistance based on the extent of deformation of the strain gauge, although other input mechanisms may be possible. In some examples, a microphone may be used to detect the tapping.

In some examples, subcutaneous device 76 may be connected via leads to the IMD 14. In other examples, subcutaneous device 76 may be leadless and instead communicate to IMD 14 via wireless telemetry through telemetry interface 46. In some examples, subcutaneous device 76 may be IMD 14 itself.

By "tapping" on subcutaneous device 76 (i.e., the control device), subcutaneous device 76 generates control device output 72 that is received by processor 42 via telemetry or leads, for example. In response to receiving control device output 72, processor 42 adjusts the delivery cycle of the electrical stimulation. Processor 42 may adjust the delivery cycle of the stimulation by accessing parameters or programs 38 stored in memory 44 of IMD. For example, in response to two "taps" by the patient, the processor may access memory 44 and determine that two "taps" corresponds to a specific therapy program (e.g., therapy program number two) that may be run to adjust the delivery cycle of the electrical stimulation. Or, in response to two "taps" by the patient, the processor may access memory 44 and determine that two "taps" corresponds to an increase (or decrease) in the delivery cycle of the electrical stimulation. In a specific example, a patient going into a meeting that may last two hours without the opportunity of a break may "tap" twice, thereby generating a control device output that is received by the processor 42. Processor 42 accesses memory 44 and determines that two "taps" corresponds, for example, to a 50% increase in the delivery cycle of the electrical stimulation. Processor 42 then adjusts the delivery cycle of the electrical stimulation such that it is increased by 50%. In another specific example, in response to receiving two "taps," processor 42 determines from memory 44 that two "taps" corresponds to "program #2" stored in programs 38. Processor 42 then proceeds to run program #2, which results in processor 42 increasing the delivery cycle of the stimulation applied by therapy delivery circuit by 50%. In yet another specific example, in response to receiving the two "taps," processor 42 directly retrieves "program #2" stored in programs 38 because the "taps" correspond directly with a program number stored in programs 38. Processor 42 then proceeds to run program #2, which results in processor 42 increasing the delivery cycle of the stimulation applied by therapy delivery circuit by 50%. Increases, or decreases, in delivery cycle may also be fixed and incremental, for example. By way of example, each "tap" may increase the delivery cycle by 10%, so one "tap" may increase the delivery cycle by 10%, two "taps" may increase the delivery cycle by 20%, etc. In this manner, the delivery cycle of the electrical stimulation delivered to the patient may be increased or decreased based upon patient input to control device 52. Hence, the delivery cycle of stimulation may be increased upon patient request and the delivery cycle of stimulation may be decreased after a voiding event and then gradually increased over time, for example.

In one example, either subcutaneous device 76 or IMD 14 may provide feedback to the patient to confirm the patient's "tapping," and thus a forthcoming change in electrical stimulation. In some examples, the feedback may be an audible sound, such as a "beep," or some other sound to confirm to the patient that a request to change the electrical stimulation ("change request") was received. In another example, the feedback may be a vibration, e.g., generated by a piezoelectric element. The feedback may occur for each "tap" provided by the patient. So, if a patient "taps" twice, two "beeps" may be provided by either subcutaneous device 76 or IMD 14. Or, feedback may occur only for the overall change request. For example, if a patient "taps" twice, only one "beep" may be provided to the patient to confirm the change request. In another example, IMD 14 may provide feedback to the patient via an external programmer such as patient programmer 24. For example, a numerical reading associated with the requested delivery cycle may be displayed on user interface 28 of patient programmer 24. Or, a confirmation of the overall change request may be displayed on user interface 28. Or, a message may be displayed confirming the change request and displaying a numerical reading associated with the requested delivery cycle.

By using subcutaneous device 76, the patient may reduce the need to use the patient programmer to change the electrical stimulation. This is of obvious benefit to the patient because not only does using subcutaneous device 76 reduce or eliminate the need for the patient to carry the patient programmer throughout the day, it also allows the patient to discreetly make the desired changes to the stimulation parameters.

FIG. 6 is a block diagram illustrating processor 42 of IMD 14 receiving an input from one or more physiological information sensing devices ("sensors"). In response to receiving a delivery cycle parameter associated with physiological information from one or more sensors, processor 42 of IMD 14 adjusts the delivery cycle of the electrical stimulation provided by therapy delivery circuit 40. Thus, IMD 14 may deliver conditional stimulation to the patient 12 via IMD 14, where, in this example, the condition is the physiological information.

In one example, accelerometer 80 may be used to sense the patient's physiological information. Accelerometers may be used to indicate a level of activity or the posture of a patient. In response to the movement or posture change of a patient, accelerometer 80 may generate a signal that corresponds to the movement or posture change. In response, processor 42 may adjust the electrical stimulation provided to the patient. Accelerometers are well known in the art and will not be described in detail in this disclosure. The use of accelerometers to sense posture is described in detail in U.S. Patent Application Publication No. 2008/0281381.

In order to adjust the delivery cycle of the electrical stimulation based on the patient's posture, accelerometer 80 may produce an output which is received by processor 42. Then, processor 42 may, for example, access memory 44 to determine the posture of the patient based on the received signal from the accelerometer, and determine which of the stored, and in some examples patient-specific, programs 38 is associated with that posture. Programs 38 may include delivery cycle parameters for processor 42 to apply to therapy deliver circuit 40. In a specific example, accelerometer 80 may generate a signal that indicates that the patient has changed positions and is now seated. Memory 44 may include program 38 that includes instructions for processor 42 to increase the delivery cycle of the electrical stimulation when the patient is seated. In such a manner, IMD 14 adjusts the delivery cycle of the electrical stimulation in response to receiving a delivery cycle parameter associated with physiological information (i.e., change in posture) from a physiological information sensing device (e.g., accelerometer).

In another example, as mentioned above, accelerometer 38 may be used to detect the activity level of the patient. Accelerometer 38 may generate one or more signals indicating a change in the level of activity of the patient. After receiving this physiological information, processor 42 may automatically titrate the cycling time of the patient. For example, the patient may go from a lower level of activity, such as walking, to a higher level of activity, such as jogging. Accelerometer 38 detects the change in the level of activity and outputs a signal to processor 42 indicative of the higher level of activity. In response to receiving this physiological information, processor 42 may automatically increase the delivery cycle of the electrical stimulation. In some examples, processor 42 increases the delivery cycle after accessing a program in memory 44. In another example, processor 42 directly increases the delivery cycle without first accessing memory 44. Processor 42 may immediately increase the delivery cycle to a specific higher delivery cycle in response to receiving a signal from the accelerometer indicating an increase in activity level. Or, processor 42 may immediately begin to increase the delivery cycle, but in a gradual fashion, thereby allowing a specific higher delivery cycle to be achieved over a period of minutes or hours.

The disclosure also contemplates examples in which the delivery cycle of the electrical stimulation may be automatically adjusted downward by processor 42 after the accelerometer detects a decrease in the patient's activity level. These examples are substantially similar to those described above with respect to an increase in the delivery cycle.

In another example of adjusting the delivery cycle of the electrical stimulation upon receiving a patient's physiological information, a bio-feedback sensor may be the source of the information. For example, if the bio-feedback sensor is used to detect bladder volume, the sensor may produce a signal once it detects that the volume of the patient's bladder has exceeded a threshold value. The signal generated by the bio-feedback sensor is received by processor 42 which then accesses memory 44 to find and run therapy program 38 that is associated with the bladder volume sensor signal. In such a manner, IMD 14 adjusts the delivery cycle of the electrical stimulation in response to receiving a delivery cycle parameter associated with physiological information from a physiological information sensing device.

Numerous sensors may be used to provide physiological information that may be used to adjust the delivery cycle of the electrical stimulation. Exemplary sensors may include sensors that measure different physiological states or conditions. For example, the sensors may include one or more of a bladder pressure sensor 82, bladder contractile force sensor 84, urinary sphincter pressure sensor 86, anal sphincter pressure sensor, urine flow rate sensor 88, urine flow pressure sensor 90, or voiding amount sensor 92. Other sensors may include muscle activity sensor 94 that monitors muscle activity of the urinary sphincter, anal sphincter, or other pelvic floor muscles. Other sensors may include nerve activity sensor 97 that monitors nerve activity of sacral nerve, pudendal nerve and its branches, or dorsal genital nerve. The sensors may be coupled by leads to IMD 14 or may wirelessly communicate with IMD 14. In some examples, one or more sensors 74 may be integral with IMD 14. In other examples, one or more sensors 74 may be part of lead 16. In other examples, one or more sensors 74 may be a part of a separate lead. In still other examples, one or more sensors 74 may be a sensing device external to IMD 14.

It should be noted that the sensors providing physiological information might be used alone or in combination to adjust the delivery cycle of the electrical stimulation. That is, processor 42 may receive an input from a first sensor indicating certain physiological information, and may simultaneously, or subsequently, receive information indicating different physiological information. Processor 42 may compare the two signals and give one signal more weight than the other, or completely disregard one of the signals, in making a decision as to how to adjust the delivery cycle of the stimulation. For example, accelerometer 80 may indicate an increased level of activity in the patient. In response, it would normally be desirable for processor 42 to increase the delivery cycle of the electrical stimulation. However, bladder volume sensor 96 may indicate that the patient's bladder is substantially empty. In this case, it may be desirable to maintain the current delivery cycle of the stimulation rather than increase the delivery cycle. Thus, processor 42 gives more weight in this instance to bladder volume sensor 96 and essentially overrides the signal from accelerometer 80.

Figure 7:
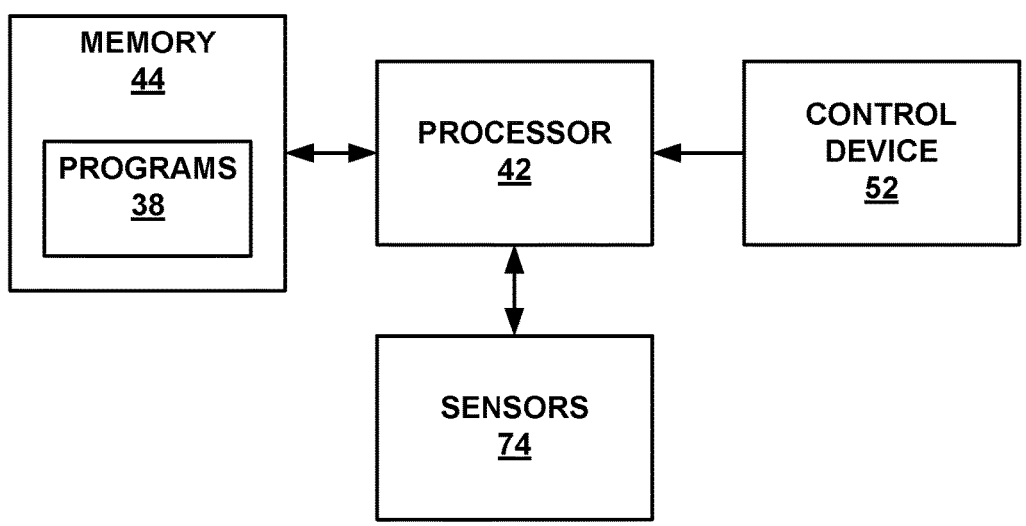
FIG. 7 is a block diagram illustrating a processor of an implantable neurostimulator in electrical communication with one or more sensors, a memory storing different time schedules, and a control device.

FIG. 7 is a block diagram illustrating processor 42 of IMD 14 in electrical communication with one or more physiological information sensors 74, memory 44 storing different programs 38 based on time schedules, and control device 52. FIG. 7 illustrates that one or more of the techniques described above may be used in combination in order to adjust the delivery cycle of the electrical stimulation delivered to by IMD 14. For example, prescribed time schedules programmed into the memory 44 may be used in combination with control device 52 in order to adjust the delivery cycle of the electrical stimulation. By way of example, a patient may have a program 38 stored in memory 44 that increases delivery cycle at 9 am on Monday through Friday, based on the patient's work schedule. On a particular Monday, for example, the patient may not be at work, due to a holiday or vacation. When the delivery cycle increases at 9 am on that particular Monday, the patient may use control device 52 to manually decrease the delivery cycle of the electrical stimulation.

In another example, the physiological information from physiological information sensing device 74 may be combined with the output from control device 52. By way of example, accelerometer 80 may indicate an increased level of activity. As such, it would normally be desirable for processor 42 to increase the delivery cycle of the electrical stimulation. However, the patient may have indicated via control device 52, such as by "tapping" above subcutaneous device 76, that the patient just voided their bladder. In this case, it may be desirable to maintain, rather than increase, the current delivery cycle of the stimulation because the bladder may be substantially empty after the voiding event. Thus, processor 42 gives more weight in this instance to control device 52 and essentially override the signal from accelerometer 80.

In an additional example, physiological information from physiological information sensing device 74 may be combined with prescribed time schedules programmed into memory 44. By way of example, the prescribed time schedule may indicate that the electrical stimulation should be increased at 9 am on Monday. However, the bladder volume sensor may indicate that the bladder is substantially empty. In this case, it may be desirable to maintain, rather than increase, the current delivery cycle of the stimulation because the bladder is known to be substantially empty. Thus, processor 42 gives more weight in this instance to the bladder volume sensor and essentially overrides the instructions associated with the time schedule in memory 44.

In another example, the physiological information from one or more physiological information sensors 74 may be combined with prescribed time schedules programmed into memory 44 as well as control device 52. By way of example, the prescribed time schedule may indicate that the electrical stimulation should be increased at 7 pm due the patient's participation on a sports team. And, at 7 pm, accelerometer 80 indicates that the patient is engaging in a higher level of activity. Based on this information, it would generally be desirable to increase the level of stimulation by increasing the delivery cycle. However, the patient may have had a voiding event just prior to 7 pm. So, at 7:15 pm, the patient may decide to "tap" the skin over the subcutaneous device in order to reduce the delivery cycle. Thus, processor 42 gives more weight in this instance to the control device and essentially overrides both the signal from accelerometer 80 and program 38 in memory 44 running based on the prescribed time schedule.

It should be noted that in all of the techniques described in this disclosure, the amplitude and frequency of the electrical stimulation may also be increased or decreased along with the changes to the delivery cycle.

The techniques described above may minimize the stimulation time of a nerve. In some aspects, the techniques described above may also increase the longevity of the device, and in particular battery longevity, and in turn reduce the frequency of surgery for device replacement. In other aspects, the techniques described above may also reduce the size of the device. And, the techniques described above may also minimize the potential side effects of chronic continuous stimulation.

Figure 8:
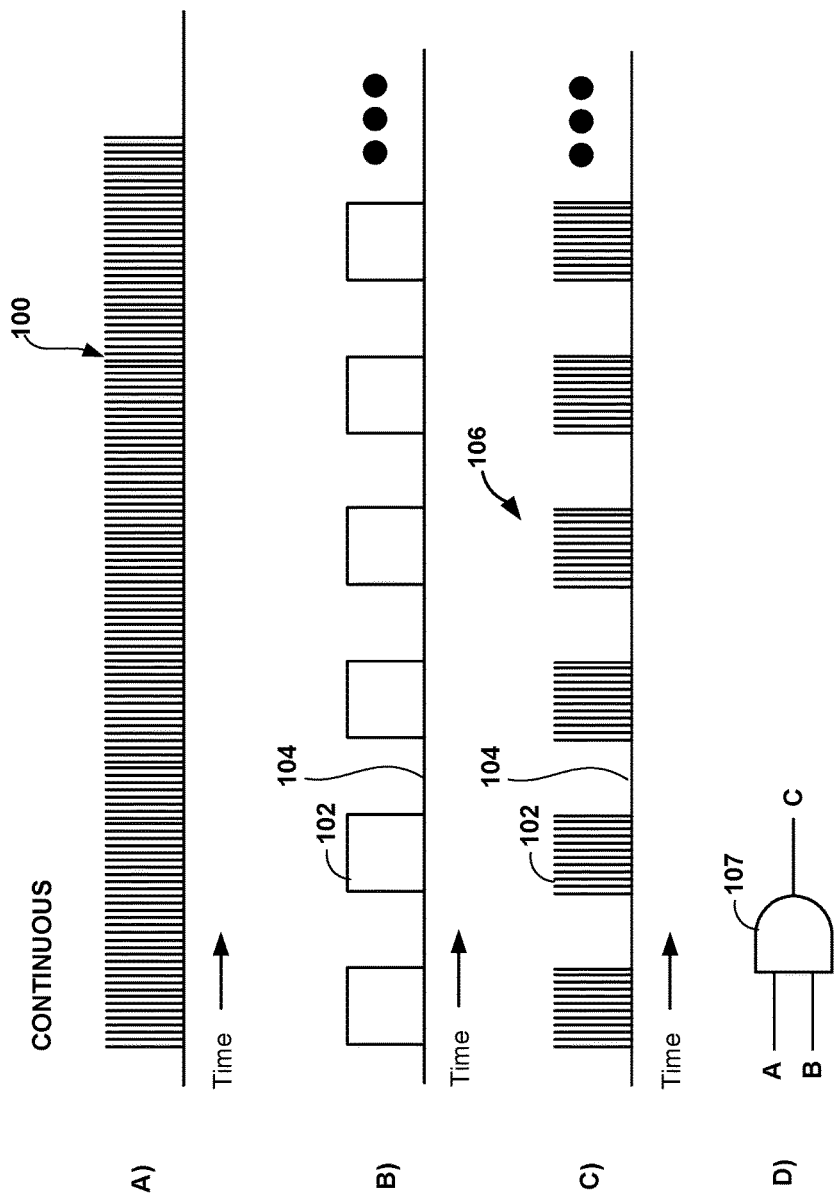
FIG. 8 is a diagram illustrating conceptually the formation of a neurostimulation pulse train.

FIG. 8 is a diagram illustrating conceptually the formation of a neurostimulation pulse train. A continuous train of pulses 100 that may be used for electrical stimulation is shown in A). A clock pulse is shown in B) with high 102 and low 104 levels. Combining the continuous train 100 of pulses in A) with the clock pulse in B) produces the train of pulses 106 shown in C). To further conceptualize, the train of pulses in C) may be produced by providing to a first input of an AND gate 107 the continuous train of pulses in A) and providing to a second input of an AND gate the clock pulse in B), as illustrated in D). When the clock pulse is high, the AND gate produces a non-zero pulse, and when the clock pulse is low, the AND gate does not produce a pulse. The delivery cycle of the train of pulses in C) is the percentage of time that the train of pulses was delivered 102 versus the total time. In C), the delivery cycle would be about 50% ON/50% OFF.

FIG. 9 depicts train of pulses 106 shown in C) in FIG. 8. In FIG. 9, the time that IMD 14 is delivering a stimulation pulse burst is represented by $T_{ON}$ and the time during which IMD 14 is not delivering a pulse burst is represented by $T_{OFF}$. The percentage of time that IMD 14 is delivering pulses is given by $T_{ON}/(T_{ON}+T_{OFF})$, and the percentage of time that IMD 14 is not delivering pulses is given by $T_{OFF}/(T_{ON}+T_{OFF})$. As seen in FIG. 9, $T_{ON}$ for the length of a pulse burst is delivered has duration $T_1$ and $T_{OFF}$ for the length of time a pulse burst is not delivered has duration $T_2$. Thus, because $T_1$ and $T_2$ are approximately equal, the delivery cycle is about 50% ON/50% OFF.

FIG. 10 depicts train of pulses 108 that has a higher delivery cycle than train of pulses 106 shown in FIG. 9. As seen in FIG. 10, $T_{ON}$ has duration $T_1$ and $T_{OFF}$ has duration $T_2$. Because $T_{ON}$, having duration $T_1$, is greater than $T_{OFF}$, having duration $T_2$, the percentage of time that IMD 14 is delivering stimulation pulses is greater than the percentage of time that IMD 14 is not delivering pulses. Hence, the delivery cycle of train of pulses 108 in FIG. 10 is higher than that of train of pulses 106 in FIG. 9. For conceptual purposes only, time $T_1$ shown in FIG. 10 may have a duration time about twice as long as the duration time $T_2$, resulting in a delivery cycle of about 66% ON/33% OFF. Increased delivery cycle, like as shown in FIG. 10, may be useful to prevent incontinence, for example, during periods of greater physical activity, when a patient is unable to void, or the like.

FIG. 11 depicts train of pulses 110 that has a lower delivery cycle than the train of pulses shown in FIGS. 9 and 10. FIG. 11 shows $T_{ON}$ with duration $T_1$ and $T_{OFF}$ with duration $T_2$. Because $T_{ON}$, is less than $T_{OFF}$, the percentage of time that IMD 14 is delivering stimulation pulses is lower than the percentage of time that IMD 14 is not delivering pulses. Hence, the delivery cycle of train of pulses 110 in FIG. 11 is lower than that of the train of pulses shown in FIGS. 9 and 10. For conceptual purposes only, time $T_1$ shown in FIG. 11 may have a duration time about a third as long as the duration time $T_2$, resulting in a delivery cycle of about 25% ON/75% OFF. Reduced delivery cycle, like as shown in FIG. 11, may be useful during periods of lower physical activity, after a patient has voided, or the like.

Figure 12:
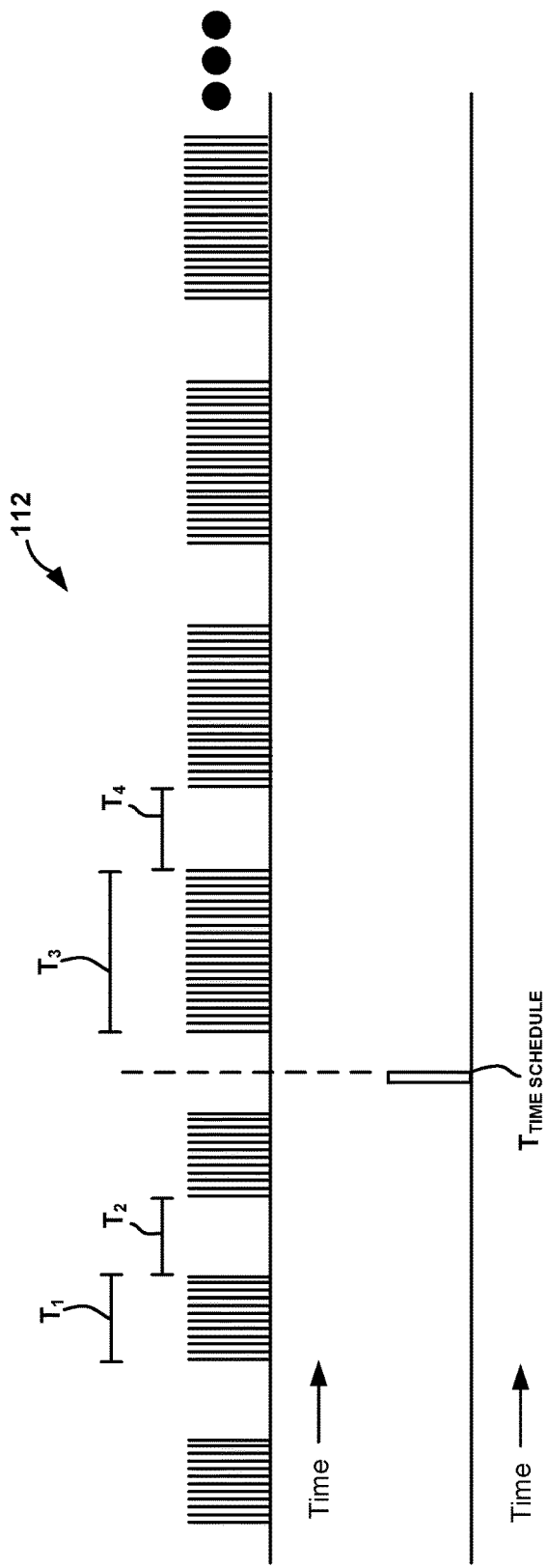
FIG. 12 depicts a train of electrical stimulation pulses delivered by an implantable neurostimulator having a delivery cycle, and in response to receiving parameters associated with a time schedule, the implantable neurostimulator adjusts the delivery cycle.

FIG. 12 depicts train of pulses 112 delivered by IMD 14 having a delivery cycle, and in response to receiving delivery cycle parameters associated with a time schedule, or an indication of time, IMD 14 adjusts the delivery cycle. In FIG. 12, train of pulses 112 initially has a first delivery cycle associated with durations $T_1$ and $T_2$. Then, in response to receiving delivery cycle parameters associated with a time schedule at time $T_{TIME\ SCHEDULE}$, processor 42 adjusts the delivery cycle. After time $T_{TIME\ SCHEDULE}$, train of pulses 112 has a second delivery cycle associated with durations $T_3$ and $T_4$. As seen graphically in FIG. 12, prior to time $T_{TIME\ SCHEDULE}$, the stimulation was ON for a duration substantially equal to the duration that stimulation was OFF. After time $T_{TIME\ SCHEDULE}$, the stimulation was ON for a longer duration than stimulation was OFF. Therefore, 1 MB 14 has varied the delivery cycle of the stimulation pulses such that the second delivery cycle is greater than the first delivery cycle.

Figure 13:
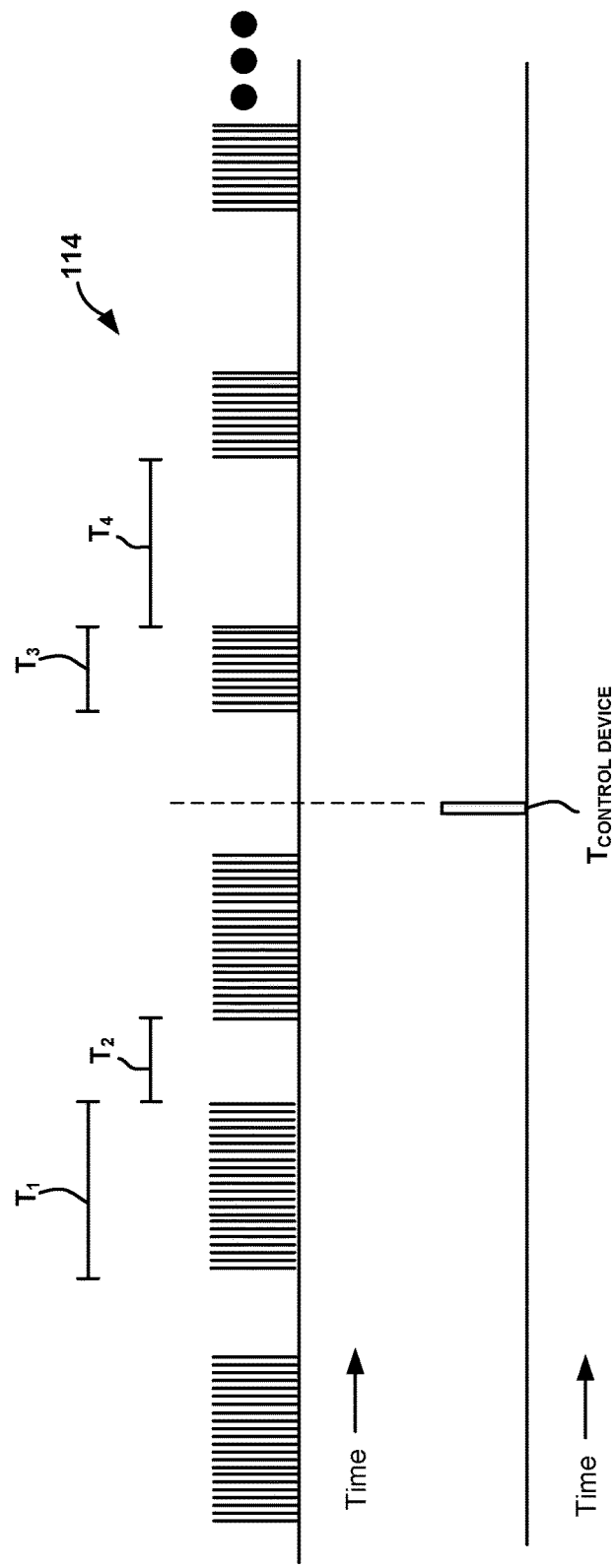
FIG. 13 depicts a train of electrical stimulation pulses delivered by an implantable neurostimulator having a delivery cycle, and in response to receiving a control device output from a control device, the implantable neurostimulator adjusts the delivery cycle.

FIG. 13 depicts train of pulses 114 delivered by IMD 14 having a delivery cycle, and in response to receiving a control device output from control device 52, IMD 14 adjusts the delivery cycle. In FIG. 13, train of pulses 114 initially has a first delivery cycle associated with durations $T_1$ and $T_2$. Then, in response to receiving a control device output from control device 52 at time $T_{CONTROL\ DEVICE}$, processor 42 adjusts the delivery cycle. For example, after voiding, a patient may use control device 52 to reduce stimulation at time $T_{CONTROL\ DEVICE}$. After time $T_{CONTROL\ DEVICE}$, train of pulses 114 has a second delivery cycle associated with durations $T_3$ and $T_4$. As seen graphically in FIG. 13, prior to time $T_{CONTROL\ DEVICE}$, the stimulation was ON for a longer duration than it was OFF, and after time $T_{CONTROL\ DEVICE}$, the stimulation was OFF for a longer duration than it was ON. Therefore, IMD 14 has varied the delivery cycle of the stimulation pulses such that the second delivery cycle is less than the first delivery cycle. Similarly, in another example, the delivery cycle may be increased in response to a patient using control device 52 to "boost" the delivery cycle. The patient may desire an increase in stimulation as the patient enters a long meeting at work, or is about to engage in greater physical activity, for example.

Figure 14:
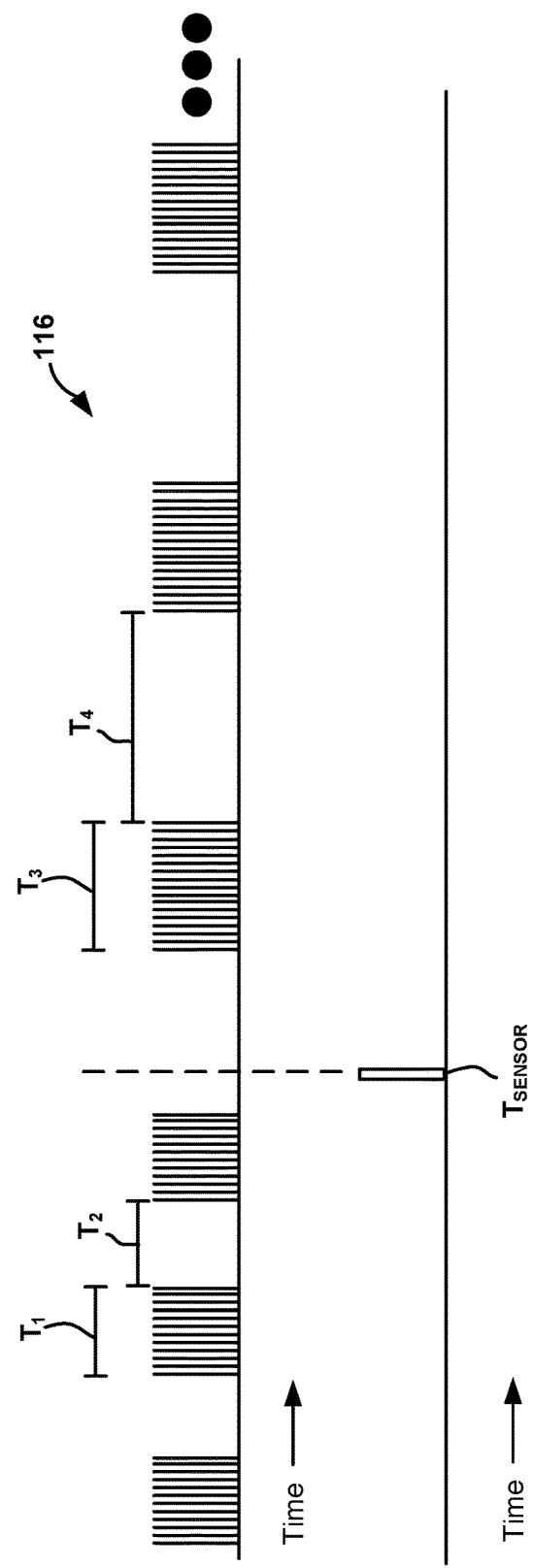
FIG. 14 depicts a train of electrical stimulation pulses delivered by an implantable neurostimulator having a delivery cycle, and in response to receiving physiological information, the implantable neurostimulator adjusts the delivery cycle.

FIG. 14 depicts train of pulses 116 delivered by IMD 14 having a delivery cycle, and in response to receiving physiological information from a physiological information sensing device ("sensor"), adjusting the delivery cycle. In FIG. 14, train of pulses 116 initially has a first delivery cycle associated with durations $T_1$ and $T_2$. Then, in response to receiving physiological information at time $T_{SENSOR}$, processor 42 adjusts the delivery cycle. After time $T_{SENSOR}$, train of pulses 116 has a second delivery cycle associated with durations $T_3$ and $T_4$. As seen graphically in FIG. 14, prior to time $T_{SENSOR}$, the stimulation was ON for a duration substantially equal to the duration that it was OFF, and after time $T_{SENSOR}$, the stimulation was OFF for a longer duration than it was ON. Therefore, IMD 14 has varied the delivery cycle of the stimulation pulses such that the second delivery cycle is less than the first delivery cycle. A patient may desire such a decrease in delivery cycle after the patient has finished voiding because less stimulation would be needed.

Figure 15:
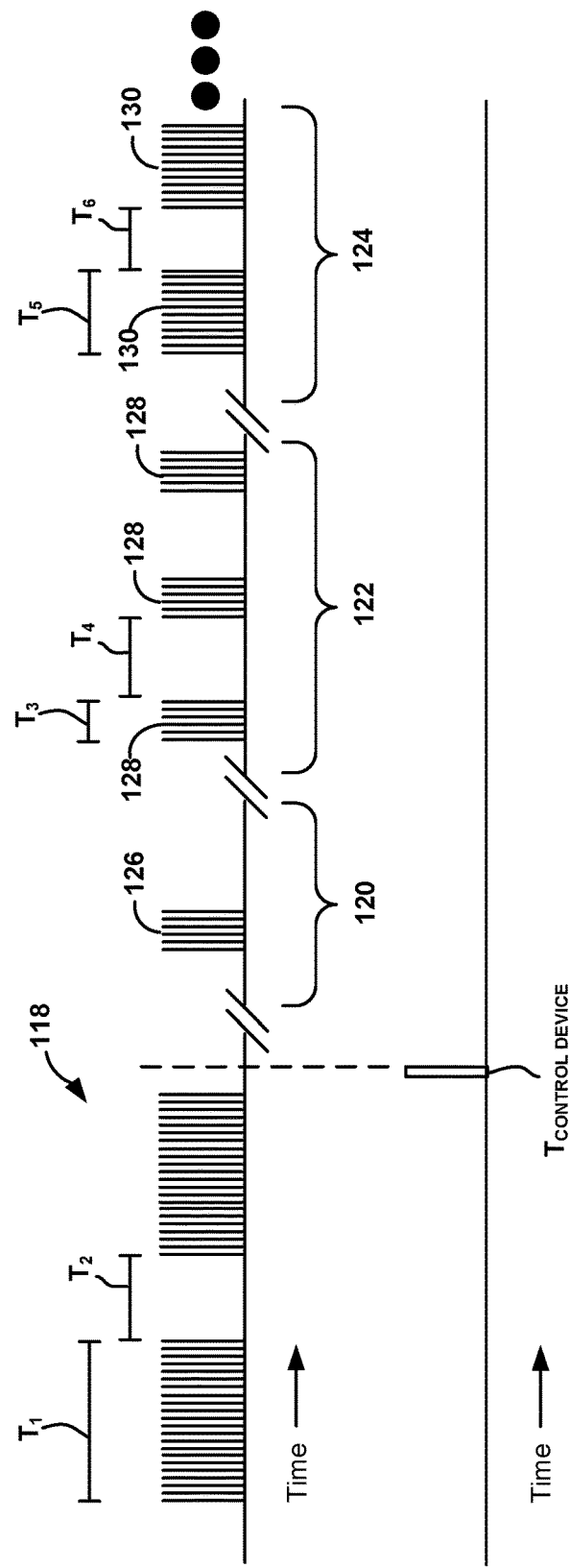
FIG. 15 depicts a train of electrical stimulation pulses delivered by an implantable neurostimulator having a delivery cycle, and in response to receiving a control device output from a control device, the implantable neurostimulator gradually increases the delivery cycle.

FIG. 15 depicts train of pulses 118 delivered by IMD 14 having a delivery cycle, and in response to receiving a control device output from control device 52, adjusting the delivery cycle. Unlike the train of pulses 114 shown in FIG. 13, the delivery cycle of the stimulation pulses in FIG. 15 gradually increases over time after receiving the control device output. This may be desirable, for example, when a patient has finished voiding. After voiding, the patient uses control device 52 to decrease the delivery cycle because less stimulation is needed immediately following a voiding event. Then, as the bladder fills over time, the delivery cycle gradually and automatically increases because more stimulation is needed. In FIG. 15, train of pulses 118 initially has a first delivery cycle associated with durations $T_1$ and $T_2$. Then, in response to receiving a control device output from control device 52 at time $T_{CONTROL\ DEVICE}$, processor 42 adjusts the delivery cycle. FIG. 15 depicts three time frames 120, 122, and 124 with electrical stimulation pulses after time $T_{CONTROL\ DEVICE}$. Of course, the choice of three time frames is merely for conceptual purposes. There may be more, or fewer, time frames in an actual implementation.

After time $T_{CONTROL\ DEVICE}$, IMD 14 stops delivering electrical stimulation pulses until time frame 120, at which time stimulation automatically resumes and a single pulse burst 126 is delivered. At a later time, during second time frame 122, IMD 14 delivers a short train of pulses (or "pulse burst"), each pulse burst denoted by 128, having a second delivery cycle associated with durations $T_3$ and $T_4$. As seen graphically in FIG. 15, the stimulation was OFF for a longer duration than it was ON during time frame 122. Then, at an even later time, during third time frame 124, IMD delivers a short train of pulses, each pulse burst denoted by 130, having a third delivery cycle associated with durations $T_5$ and $T_6$. As mentioned above, a gradual increase in delivery cycle over time after a voiding event may be desirable to automatically account for the increased stimulation needs of the patient as the patient's bladder fills, for example. As further seen graphically in FIG. 15, the stimulation was ON for a longer duration than it was OFF during time frame 124.

In this manner, processor 42 adjusts the delivery cycle of the electrical stimulation pulse in response to receiving a control device output from a control device at time $T_{CONTROL\ DEVICE}$. Additionally, processor 42 turns off stimulation for a certain period of time after receiving a control device output from a control device, then automatically resumes after a certain period of time, gradually increasing the delivery cycle of the electrical stimulation pulse. Turning off stimulation for a certain period of time may be desirable after a voiding event, for example, because a patient no longer immediately needs stimulation. Then, a gradual increase in delivery cycle over time after a voiding event may be desirable to automatically account for the increased stimulation needs of the patient as the patient's bladder fills, for example. In one example, the control device output from control device 52 at time $T_{CONTROL\ DEVICE}$ may be the result of patient "tapping" the skin after a voiding event. In that case, the patient may want to turn off stimulation after the voiding event, but gradually allow it to increase over time automatically. In some examples, there may be an "offset" in the decrease in delivery cycle after the request for a decrease. For example, the delivery cycle prior to a request for decrease may be 50% ON, but immediately after the request the delivery cycle may increase to 60% ON, for example, and then automatically and gradually increase over time to 20%.

Figure 16A:
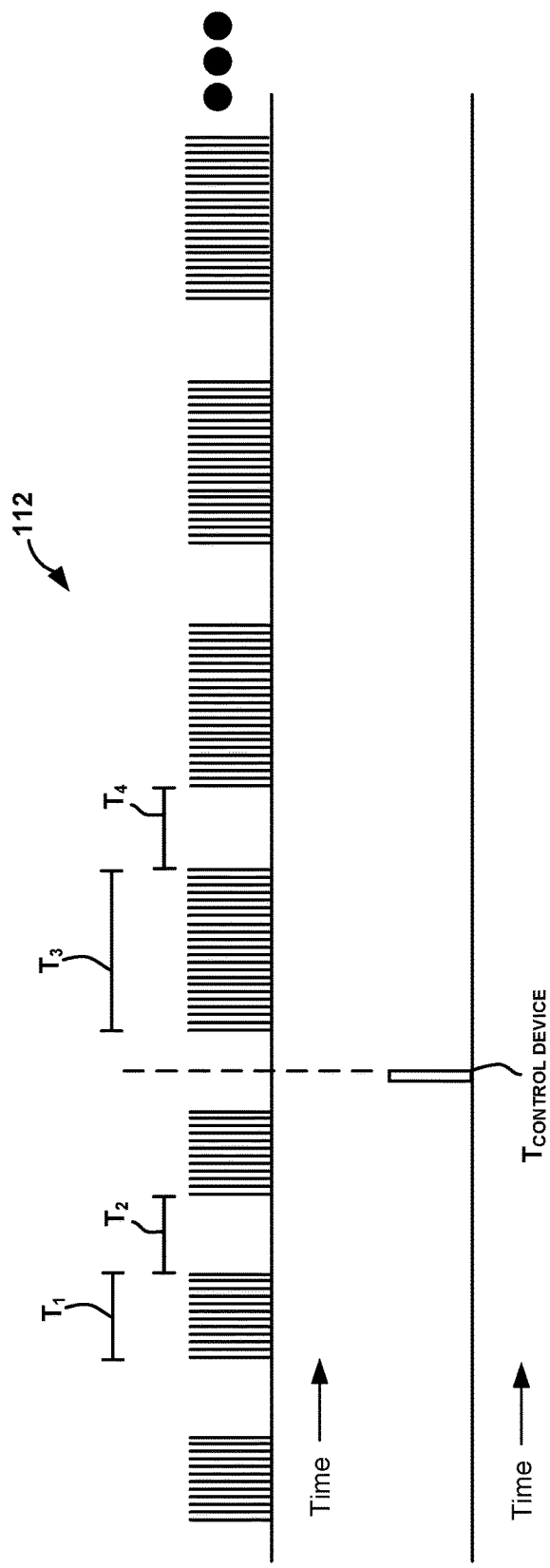
FIG. 16A depicts a train of electrical stimulation pulses delivered by an implantable neurostimulator having a delivery cycle, and in response to receiving a control device output from a control device, the implantable neurostimulator increases the delivery cycle.

FIG. 16A depicts train of pulses 112 delivered by IMD 14 having a delivery cycle, and in response to receiving a control device output from control device 52, IMD 14 adjusts the delivery cycle. In FIG. 16A, train of pulses 112 initially has a first delivery cycle associated with durations $T_1$ and $T_2$. Then, in response to receiving a control device output from control device 52 at time $T_{CONTROL\ DEVICE}$, processor 42 adjusts the delivery cycle. After time $T_{CONTROL\ DEVICE}$, train of pulses 112 has a second delivery cycle associated with durations $T_3$ and $T_4$. As seen graphically in FIG. 16A, prior to time $T_{CONTROL\ DEVICE}$, the stimulation was ON for a duration substantially equal to the duration that stimulation was OFF. After the patient has requested an increase via a manual input of control device 52 at time $T_{CONTROL\ DEVICE}$, the stimulation was ON for a longer duration than stimulation was OFF. Therefore, IMD 14 has adjusted the delivery cycle of the stimulation pulses such that the second delivery cycle is greater than the first delivery cycle. It may be desirable for a patient to increase the delivery cycle and thereby provide a "boost" of delivery cycle when the patient is about to engage in greater physical activity, when the patient is entering a meeting and will not have an opportunity to void for an extended period of time, or the like. In some examples, there may be an "offset" in the increase in delivery cycle after the request for an increase. For example, the delivery cycle prior to a request for increase may be 30% ON, but immediately after the request the delivery cycle may decrease to 20% ON, for example, and then automatically and gradually increase over time to 80%.

Figure 16B:
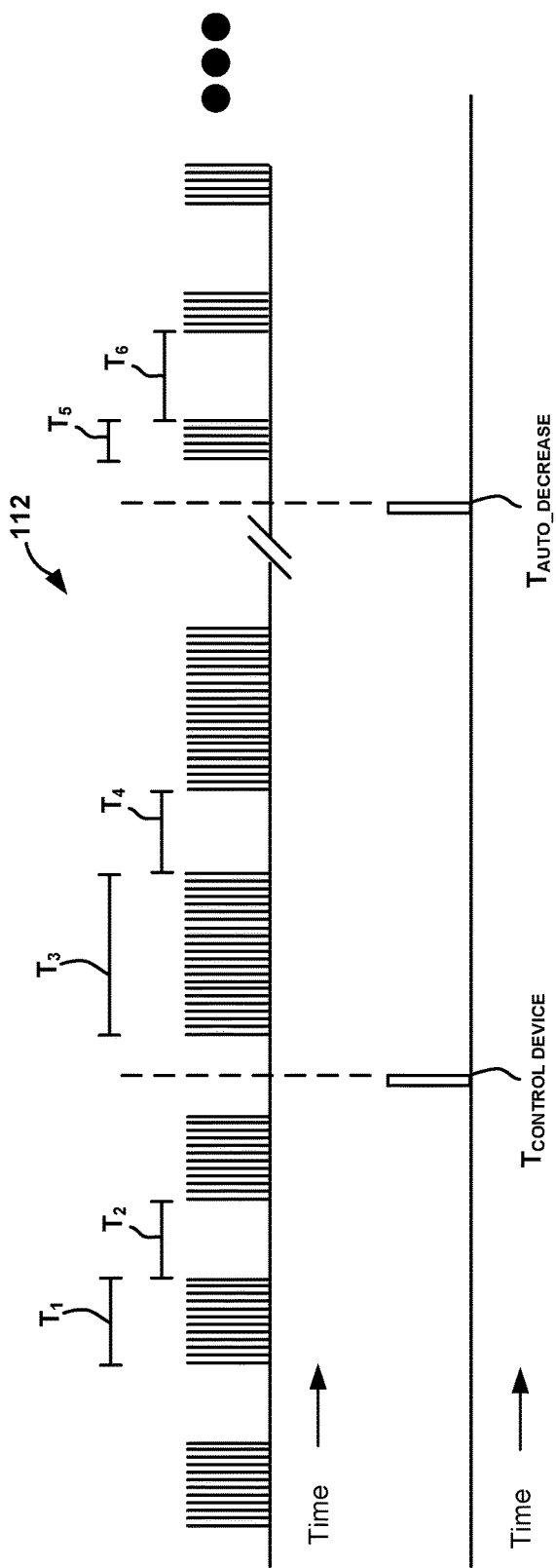
FIG. 16B depicts a train of electrical stimulation pulses delivered by an implantable neurostimulator having a delivery cycle, and in response to receiving a control device output from a control device, the implantable neurostimulator increases the delivery cycle, then after a time automatically decreases the delivery cycle.

FIG. 16B is similar to FIG. 16A, depicting train of pulses 112 delivered by IMD 14 having a delivery cycle, and in response to receiving a control device output from control device 52, IMD 14 adjusts the delivery cycle. However, in FIG. 16B the delivery cycle of the stimulation automatically decreases at time $T_{AUTO\_DECREASE}$. In FIG. 16B, train of pulses 112 initially has a first delivery cycle associated with durations $T_1$ and $T_2$. Then, in response to receiving a control device output from control device 52 at time $T_{CONTROL\ DEVICE}$, processor 42 adjusts the delivery cycle. After time $T_{CONTROL\ DEVICE}$, train of pulses 112 has a second delivery cycle associated with durations $T_3$ and $T_4$. As seen graphically in FIG. 16B, prior to time $T_{CONTROL\ DEVICE}$, the stimulation was ON for a duration substantially equal to the duration that stimulation was OFF. After the patient has requested an increase via a manual input of control device 52 at time $T_{CONTROL\ DEVICE}$, the stimulation was ON for a longer duration than stimulation was OFF. Then, after time $T_{AUTO\_DECREASE}$, the delivery cycle of the stimulation automatically decreases. After time $T_{AUTO\_DECREASE}$, train of pulses 112 has a third delivery cycle associated with durations $T_5$ and $T_6$. As seen graphically in FIG. 16B, after time $T_{AUTO\_DECREASE}$, the stimulation was OFF for a longer duration than stimulation was ON. Time $T_{AUTO\_DECREASE}$ may be a predetermined time delay that occurs some time after time $T_{CONTROL\ DEVICE}$, and may be a parameter stored within one of programs 38, for example. In some examples, the delivery cycle may automatically decrease to a pre-defined delivery cycle level. Or, in other examples, the delivery cycle may automatically decrease to the level of the delivery cycle prior to the "boost" in delivery cycle. In some examples, the delivery cycle may decrease immediately to a lower delivery cycle, as in FIG. 16B. In other examples, the delivery cycle may decrease gradually to a lower delivery cycle. Automatically decreasing the delivery cycle may be desirable in the event that the patient forgets to reduce the level.

Figure 17:
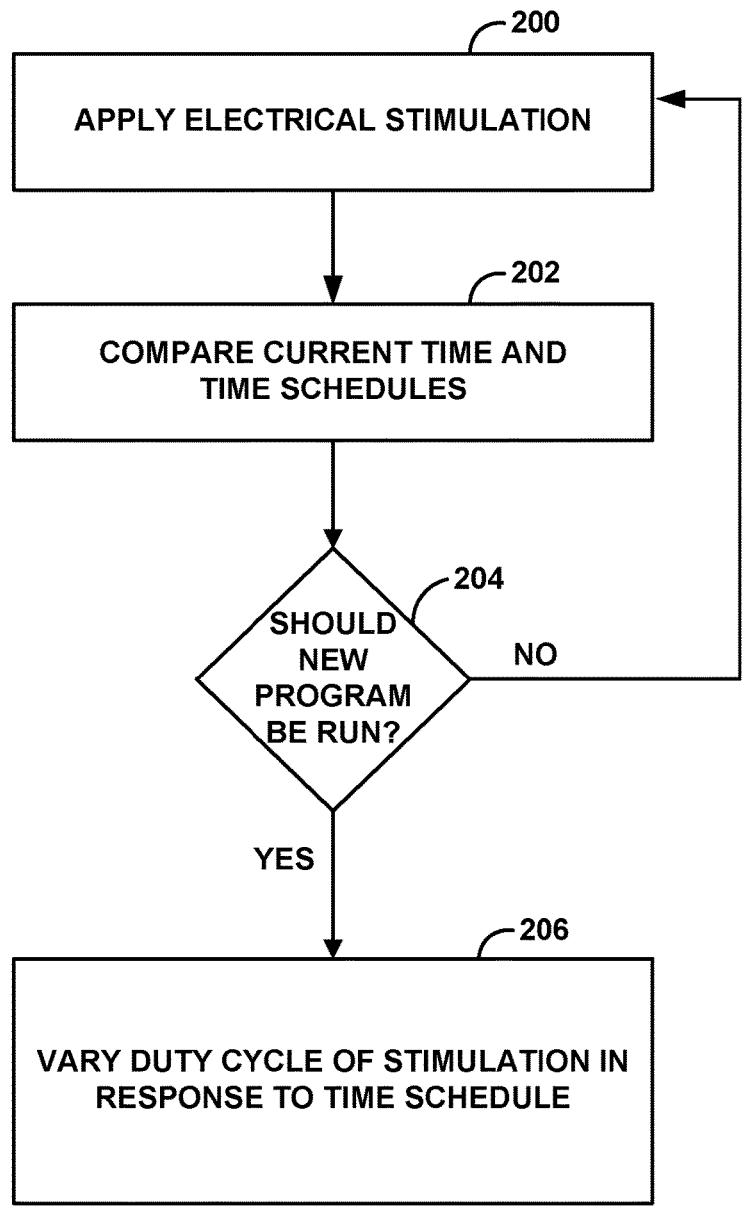
FIGS. 17-20 are flow diagrams illustrating methods of electrically stimulating a nerve via an implanted device in accordance with this disclosure.

FIG. 17 is a flow diagram illustrating a method of electrically stimulating a target site via an implanted device in accordance with this disclosure. In the example of FIG. 17, electrical stimulation is applied via IMD 14 to a patient (200). IMD 14, and in particular processor 42, receives the current time from timing device 52, and compares the current time to the time schedules stored in memory 44 (202). If a new program should be run based on the current time (204), or if the same program is run with only a change to the delivery cycle, then the delivery cycle of the electrical stimulation is adjusted in response to the time schedule (206). The delivery cycle may be increased or decreased, depending on the circumstances. If the current time does not indicate that a new program should be run (204), IMD 14 continues to apply stimulation (200) without adjusting the delivery cycle.

Figure 18:
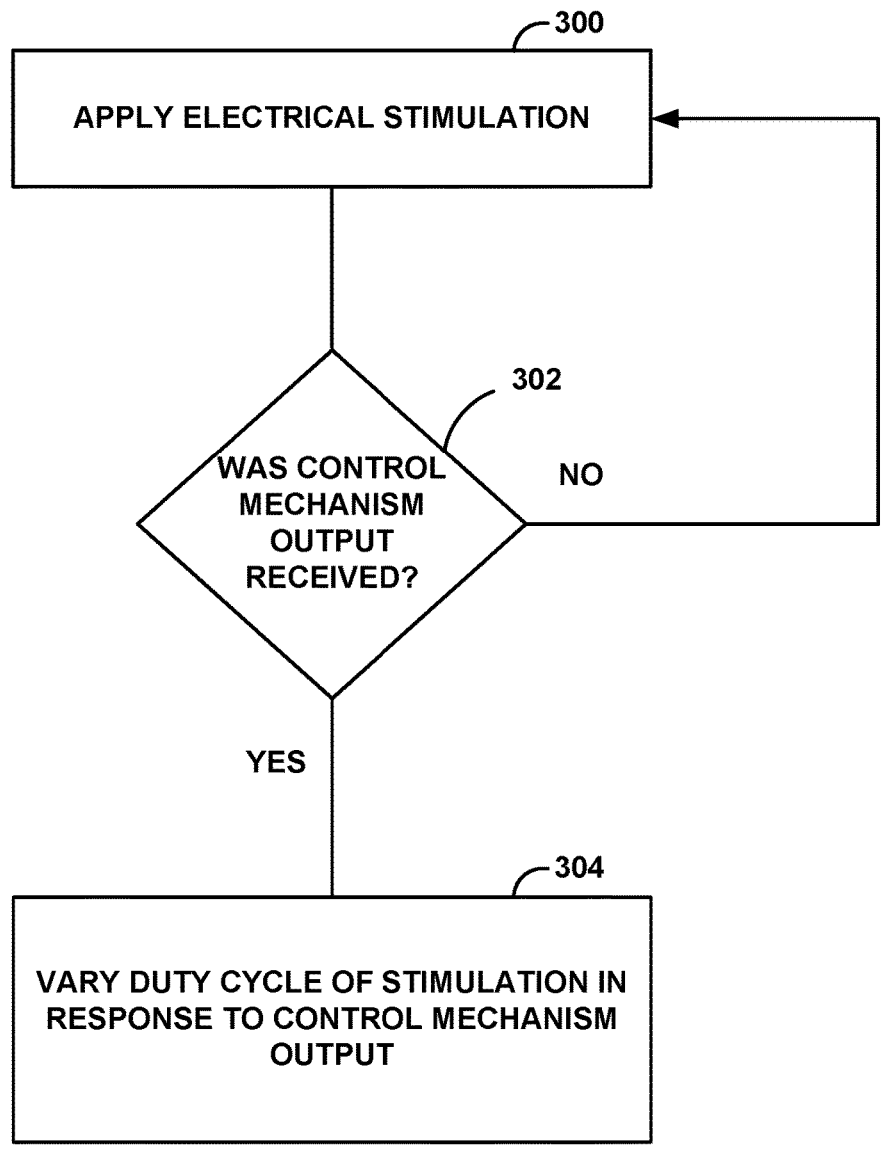

FIG. 18 is a flow diagram illustrating another method of electrically stimulating a target site via an implanted device in accordance with this disclosure. In the example of FIG. 18, electrical stimulation is applied via IMD 14 to a patient (300). If a control device output was received (302) by IMD 14, and in particular processor 42, the delivery cycle of the electrical stimulation is adjusted (304). The delivery cycle may be increased or decreased, depending on the circumstances. If a control device output was not received (302), IMD 14 continues to apply stimulation (300) without adjusting the delivery cycle.

Figure 19:
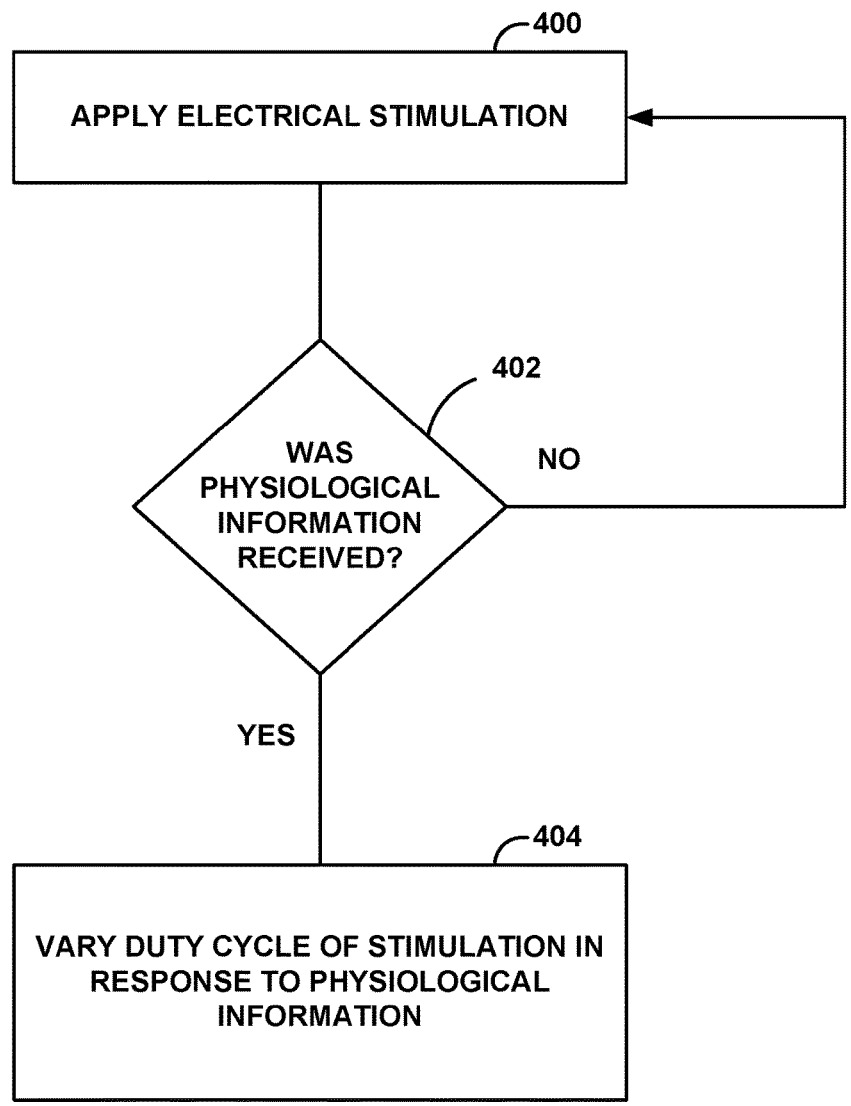

FIG. 19 is a flow diagram illustrating an additional method of electrically stimulating a target site via an implanted device in accordance with this disclosure. In the example of FIG. 19, electrical stimulation is applied via IMD 14 to a patient (400). If physiological information from physiological information sensing device 74 was received (402) by IMD 14, and in particular processor 42, the delivery cycle of the electrical stimulation is adjusted (404). The delivery cycle may be increased or decreased, depending on the circumstances. If physiological information was not received (402), IMD 14 continues to apply stimulation (400) without adjusting the delivery cycle.

Figure 20:
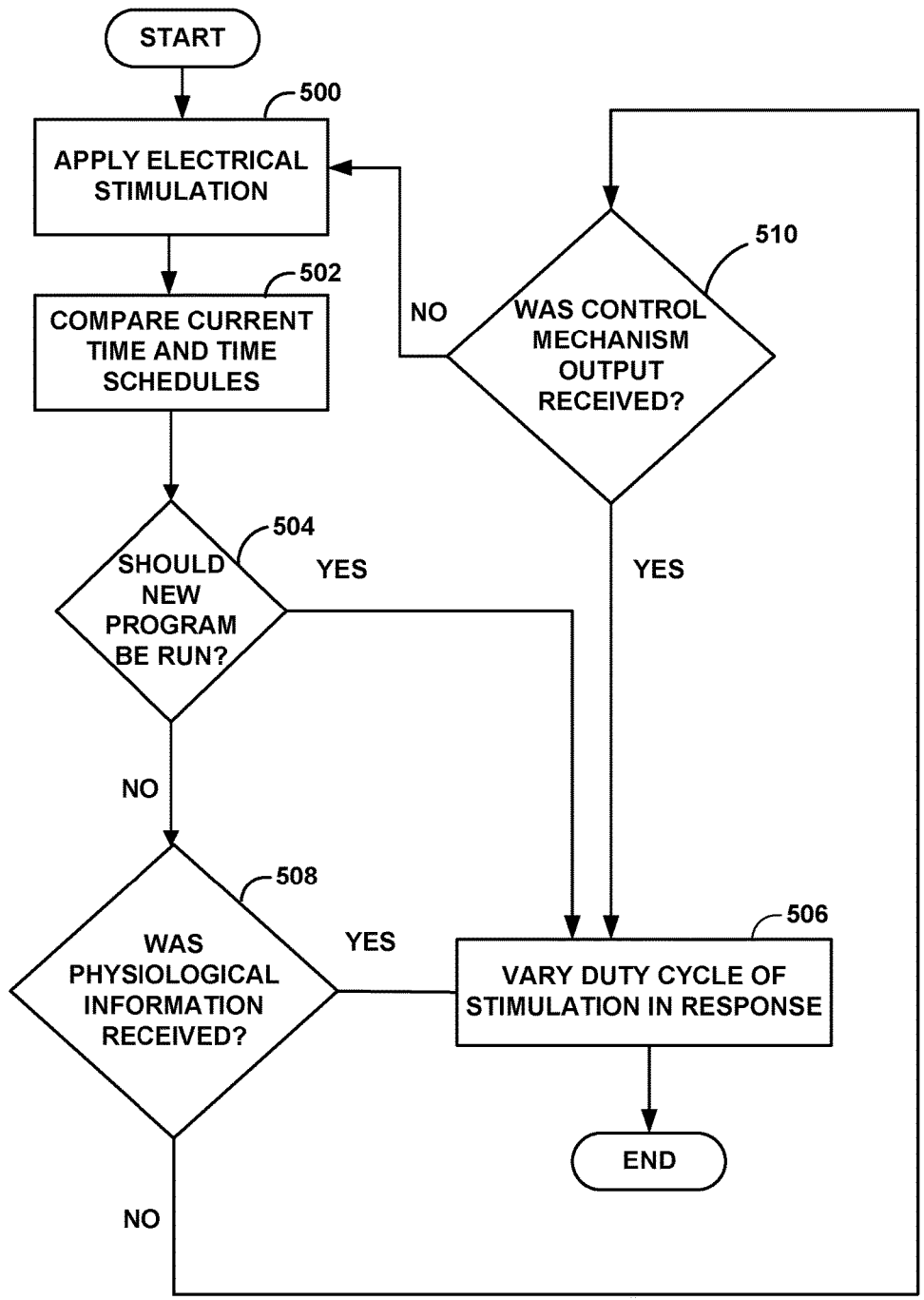

FIG. 20 is a flow diagram illustrating another method of electrically stimulating a target site via an implanted device in accordance with this disclosure. In the example of FIG. 20, the methods shown in FIGS. 17-19 have been combined to illustrate that these methods may be used in combination with one another. Electrical stimulation is applied via IMD 14 to a patient (500). IMD 14, and in particular processor 42, receives the current time from timing device 54, and compares the current time to the time schedules stored in memory 44 (502). If a new program should be run based on the current time (504), then the delivery cycle of the electrical stimulation is varied in response to the time schedule (506). If the current time does not indicate that a new program should be run (504), processor 42 determines whether physiological information from physiological information sensing device 74 was received (508). If physiological information was received, the delivery cycle of the electrical stimulation is varied (506). If physiological information was not received (508), processor 42 determines whether a control device output was received (510) from control device 52. If a control device output was received, the delivery cycle of the electrical stimulation is varied (506). If a control device output was not received (510), IMD 14 continues to apply stimulation (500) without adjusting the delivery cycle.

The techniques of this disclosure may leverage any carry-over effect after stimulation has ended. The term "carry-over effect" generally refers to the effect of stimulation continuing on to some degree past the time that stimulation ended. This carry-over effect is the reason that a continuous train of pulses, such as the one shown in A) of FIG. 8, may not be needed in order to provide adequate stimulation to a patient. The carry-over effect causes the nerve, muscle, or other area of stimulation to retain the effects of stimulation beyond the time that stimulation was applied. By way of example, if an electrical stimulation pulse train, such as shown in FIG. 9, is delivered to a target area, the target area will be maximally stimulated during the time that the non-zero pulse is applied. However, during the time that there is no pulse, the target area retains some of the effect of the initial stimulation. However, the effect decreases over time until a non-zero pulse is again applied to the nerve.

During the period that the nerve receives the non-zero pulse, the target area experiences maximum stimulation effect $STIM_{MAX}$. Immediately after the non-zero pulse ends, the target area continues to experience a stimulation effect $STIM_3$, a result of the carry-over effect, where $STIM_{MAX} > STIM_3$. Some period of time later, the target area continues to experience a stimulation effect $STIM_2$, also a result of the carry-over effect, where $STIM_3 > STIM_2$. And, at a period of time immediately before the non-zero pulse is again applied, the target area continues to experience a stimulation effect $STIM_1$, also a result of the carry-over effect, where $STIM_2 > STIM_1$. If enough time elapses before another non-zero pulse is applied, the target area will no longer experience a sufficient stimulation effect. By leveraging the carry-over effect, IMD 14 may minimize the stimulation time needed to stimulate the patient. That is, by allowing the stimulation effect between pulses or pulse bursts to decrease, or decay, to a level that is below the maximum stimulation effect but above some level that will result in incontinence or other symptoms, the stimulation time needed to stimulate the patient may be minimized.

With reference to the description above, a patient that is at rest with a half full bladder may only require a stimulation effect of $STIM_1$ before another electrical stimulation pulse is required to prevent incontinence, for example. The same patient that is jogging with a half full bladder, however, may require a stimulation effect of $STIM_2$ before another electrical stimulation pulse is required to prevent incontinence. As mentioned above, $STIM_2 > STIM_1$, so the patient that is jogging may require a pulse having a higher delivery cycle then when patient at rest. In this manner, the carry-over effects of stimulation may be leveraged to minimize the stimulation time of a nerve. As a consequence, leveraging the carry-over effects may also increase the longevity of the device, and in particular battery longevity. And, leveraging the carry-over effects may also reduce the size of the device and minimize the potential side effects of chronic continuous stimulation.

The techniques described in this disclosure may reduce the stimulation time of a nerve. The techniques described above may also increase the longevity of the device, and in particular battery longevity. The technique described above may also reduce the frequency of surgery for device replacement. The techniques described above may also reduce the size of the device. The techniques described in this disclosure may also minimize the potential side effects of chronic continuous stimulation. By adjusting the delivery cycle of electrical stimulation at least partially to provide conditional electrical stimulation, the overall amount of stimulation applied to the patient may be reduced, in comparison to continuous stimulation. With a reduced amount of stimulation, the patient may be less susceptible to undesirable side effects of electrical stimulation, such as nerve fatigue, accommodation, habituation or desensitization. In addition, delivery of conditional stimulation instead of continuous stimulation may reduce power consumption and thereby conserve power. Reduced power consumption may promote device longevity, permit reduction in power source size and overall IMD size, and extend the time between recharge cycles, if applicable.

The techniques described in this disclosure may be implemented in hardware, software, firmware, or any combination thereof. In particular, the techniques may be implemented in a hardware device, such as a wireless communication device or network device, either of which may include software and/or firmware to support the implementation. For portions implemented in software, the techniques may be realized in part by an article of manufacture such as a computer-readable storage medium comprising program code containing instructions that, when executed, performs one or more of the methods described above. In this case, the computer-readable storage medium may comprise random access memory (RAM) such as synchronous dynamic random access memory (SDRAM), read-only memory (ROM), non-volatile random access memory (NVRAM), electrically erasable programmable read-only memory (EEPROM), FLASH memory, magnetic or optical data storage media, and the like. In one example, the computer-readable storage medium does not comprise a carrier signal or a propagated wave. In another example, rather than being stored, computer-readable instructions may be embodied on a computer-readable medium such as a carrier signal or propagated wave.

The program code may be executed by one or more processors, such as one or more digital signal processors (DSPs), general purpose microprocessors, an application specific integrated circuits (ASICs), field programmable logic arrays (FPGAs), or other equivalent integrated or discrete logic circuitry. In this sense, the techniques are implemented in hardware, whether implemented entirely in hardware or in hardware such as a processor executing computer-readable code.

The code may be executed by one or more processors, such as one or more digital signal processors (DSPs), general purpose microprocessors, an application specific integrated circuits (ASICs), field programmable logic arrays (FPGAs), or other equivalent integrated or discrete logic circuitry. Accordingly, the term "processor," as used herein may refer to any of the foregoing structure or any other structure suitable for implementation of the techniques described herein.

The following description refers to example implementations of the techniques of this disclosure. In one example, a method comprises applying electrical stimulation from an electrical stimulation device to a patient, and adjusting a delivery cycle of the electrical stimulation in response to a time in a time schedule. The method may further comprise applying the stimulation to a peripheral nerve of the patient. In some examples, the peripheral nerve may be at least one of a sacral nerve, a pudendal nerve, branches associated with the pudendal nerve, or a dorsal genital nerve.

In one example, the delivery cycle is one of a ratio of a first time duration of each pulse that is delivered to a second time duration between successive pulses or a ratio of a first time duration of a pulse train comprising a pulse burst is delivered to a second time duration between successive pulse bursts.

In one example, adjusting a delivery cycle comprises adjusting the delivery cycle based on a stored delivery cycle parameter associated with the time.

In some examples, the time schedule is selected from the group consisting of a fixed cycling pattern, a time schedule that varies according to the time of day, a time schedule that varies according to a circadian rhythm, and a time schedule that varies according to a weekly pattern indicating patient-specific delivery cycle settings for specific days of the week.

In other examples, the method may further comprise adjusting the delivery cycle of the electrical stimulation in response to user input from a control device. In some examples, the method may further comprise adjusting the delivery cycle of the electrical stimulation in response to physiological information from a physiological information sensing device.

In one example, adjusting the delivery cycle comprises increasing the delivery cycle automatically over time without manual user intervention. In other examples, adjusting the delivery cycle comprises decreasing the delivery cycle automatically over time without manual user intervention.

In some examples, applying electrical stimulation comprises applying electrical stimulation according to a pre-programmed pattern. In one example, the pre-programmed pattern is selected based on one or more patient-specific criteria.

In one example, the electrical stimulation is selected to alleviate at least one of urinary incontinence, fecal incontinence, sexual dysfunction, and pelvic pain.

In another example, a method comprises applying electrical stimulation from an electrical stimulation device to a patient, and adjusting a delivery cycle of the electrical stimulation in response to user input. The method may further comprise applying the stimulation to a peripheral nerve of the patient. In some examples, the peripheral nerve may be at least one of a sacral nerve, a pudendal nerve, branches associated with the pudendal nerve, or a dorsal genital nerve.

In some examples, the method may further comprise increasing or decreasing the delivery cycle automatically in response to receiving the user input. In other examples, the method may comprise decreasing the delivery cycle gradually after a time delay after receiving the user input. In some examples, the method may comprise decreasing the delivery cycle automatically in response to receiving the user input, and increasing the delivery cycle gradually. In one example, the method may comprise increasing the delivery cycle gradually in response to receiving the user input.

In another example, the method may include adjusting the delivery cycle of the electrical stimulation in response to physiological information from a physiological information sensing device.

In another example, a method comprises applying electrical stimulation from an electrical stimulation device to a patient, and adjusting a delivery cycle of the electrical stimulation in response to physiological information from a physiological information sensing device. The method may further comprise applying the stimulation to a peripheral nerve of the patient. In some examples, the peripheral nerve may be at least one of a sacral nerve, a pudendal nerve, branches associated with the pudendal nerve, or a dorsal genital nerve.

In one example, the physiological information relates to an activity level of a patient. In some examples, the method further comprises increasing the delivery cycle when the activity level increases.

In another example, the physiological information relates to at least one of a posture of a patient, bladder pressure, bladder contractile force, urinary sphincter pressure, anal sphincter pressure, urine flow rate, urine flow pressure, voiding amount, muscle activity, and nerve activity.

In some examples, the electrical stimulation is applied automatically in response to the physiological information without manual user intervention.

In one example, applying electrical stimulation comprises applying the electrical stimulation according to a pre-programmed pattern. In some examples, the pre-programmed pattern is selected based on one or more patient-specific criteria.

In some examples, the sensing device is an accelerometer. In one example, the accelerometer is a multi-axis accelerometer.

In other examples, adjusting the delivery cycle comprises increasing the delivery cycle automatically over time without manual user intervention. In some examples, adjusting the delivery cycle comprises decreasing the delivery cycle automatically over time without manual user intervention.

Many examples of the disclosure have been described. These and other examples are within the scope of the following claims. Various modifications may be made without departing from the scope of the claims.

The invention claimed is:

1. A system comprising:
a therapy delivery circuit configured to apply a plurality of electrical stimulation pulse trains from an electrical stimulation device to a patient; and
one or more processors configured to:
cause the therapy delivery circuit to apply, according to a first delivery cycle, a first plurality of electrical stimulation pulse trains from an electrical stimulation device to a patient, wherein each electrical stimulation pulse train of the first plurality of electrical stimulation pulse trains comprises a series of pulses, wherein the first delivery cycle of the first plurality of electrical stimulation pulse trains is a first ratio of a first time duration during which the electrical stimulation pulse train of the first plurality of electrical stimulation pulse trains is delivered to a second time duration between successive electrical stimulation pulse trains of the first plurality of electrical stimulation pulse trains;
receive at least one of a user input or physiological information from a physiological information sensing device;
cause the therapy delivery circuit to apply, according to a second delivery cycle and in response to the at least one of the user input or the physiological information, a second plurality of electrical stimulation pulse trains from the electrical stimulation device to the patient, wherein each electrical stimulation pulse train of the second plurality of electrical stimulation pulse trains comprises a series of pulses, wherein the second delivery cycle of the second plurality of electrical stimulation pulse trains is a second ratio of a first time duration during which the electrical stimulation pulse train of the second plurality of electrical stimulation pulse trains is delivered to a second time duration between successive electrical stimulation pulse trains of the second plurality of electrical stimulation pulse trains and is different than the first delivery cycle; and
cause the therapy delivery circuit to automatically change, over at least three electrical stimulation pulse trains, the second delivery cycle to a third delivery cycle different than the second delivery cycle, wherein each electrical stimulation pulse train of the at least three electrical stimulation pulse trains comprises a plurality of pulses, and wherein the third delivery cycle is a third ratio of a first time duration during which a final electrical stimulation pulse train of the at least three electrical stimulation pulse trains is delivered to a second time duration between successive electrical stimulation pulse trains of the at least three electrical stimulation pulse trains.

2. The system of claim 1, wherein the one or more processors is configured to cause the therapy delivery circuit to automatically change, over at least three electrical stimulation pulse trains, the second delivery cycle to the third delivery cycle by at least:
causing the therapy delivery circuit to at least one of automatically increase, over the at least three electrical stimulation pulse trains, the delivery cycle of the electrical stimulation pulse train or automatically decrease, over the at least three electrical stimulation pulse trains, the delivery cycle of the electrical stimulation pulse train.

3. The system of claim 1, wherein the therapy delivery circuit is configured to apply the electrical stimulation pulse trains from the electrical stimulation device to at least one of a sacral nerve, a pudendal nerve, or a dorsal genital nerve of the patient to alleviate a pelvic floor disorder of the patient.

4. The system of claim 1, further comprising an implantable medical device, wherein the implantable medical device comprises the one or more processors and the therapy delivery circuit.

5. The system of claim 1, further comprising an implantable medical device and a programmer, wherein the implantable medical device comprises the therapy delivery circuit and the programmer comprises the one or more processors.

6. The system of claim 1, wherein the at least one of the user input or the physiological information comprises an indication of a voiding or defecation event.

7. The system of claim 1, wherein a pulse duty cycle is substantially unchanged between a first electrical stimulation pulse train of the at least three electrical stimulation pulse strains and a last electrical stimulation pulse train of the at least three electrical stimulation pulse trains.

8. The system of claim 1, further comprising an implantable medical lead configured to be coupled to the therapy delivery circuit.

9. A device comprising:
means for applying, according to a first delivery cycle, a first plurality of electrical stimulation pulse trains to a patient, wherein each electrical stimulation pulse train of the first plurality of electrical stimulation pulse trains comprises a series of pulses, wherein the first delivery cycle of the first plurality of electrical stimulation pulse trains is a first ratio of a first time duration during which the electrical stimulation pulse train of the first plurality of electrical stimulation pulse trains is delivered to a second time duration between successive electrical stimulation pulse trains of the first plurality of electrical stimulation pulse trains;
means for receiving at least one of a user input or physiological information from a physiological information sensing device;

means for applying, according to a second delivery cycle and in response to the at least one of the user input or the physiological information, a second plurality of electrical stimulation pulse trains to the patient, wherein each electrical stimulation pulse train of the second plurality of electrical stimulation pulse trains comprises a series of pulses, wherein the second delivery cycle of the second plurality of electrical stimulation pulse trains is a second ratio of a first time duration during which the electrical stimulation pulse train of the second plurality of electrical stimulation pulse trains is delivered to a second time duration between successive electrical stimulation pulse trains of the second plurality of electrical stimulation pulse trains and is different than the first delivery cycle; and means for automatically changing, over at least three electrical stimulation pulse trains, the second delivery cycle to a third delivery cycle different than the second delivery cycle, wherein each electrical stimulation pulse train of the at least three electrical stimulation pulse trains comprises a plurality of pulses, and wherein the third delivery cycle is a third ratio of a first time duration during which a final electrical stimulation pulse train of the at least three electrical stimulation pulse trains is delivered to a second time duration between successive electrical stimulation pulse trains of the at least three electrical stimulation pulse trains.

10. The device of claim 9, wherein the means for automatically changing, over at least three electrical stimulation pulse trains, the second delivery cycle to the third delivery cycle comprises:

means for causing at least one of automatically increasing, over the at least three electrical stimulation pulse trains, the delivery cycle of the electrical stimulation pulse train or automatically decreasing, over the at least three electrical stimulation pulse trains, the delivery cycle of the electrical stimulation pulse train.

11. The device of claim 9, wherein the means for applying the first plurality of electrical stimulation pulse trains and the means for delivering the second plurality of electrical stimulation pulse trains are configured to apply the electrical stimulation pulse trains from the electrical stimulation device to at least one of a sacral nerve, a pudendal nerve, or a dorsal genital nerve of the patient to alleviate a pelvic floor disorder of the patient.

12. The device of claim 9, wherein the at least one of the user input or the physiological information comprises an indication of a voiding or defecation event.

13. The device of claim 9, wherein a pulse duty cycle is substantially unchanged between a first electrical stimulation pulse train of the at least three electrical stimulation pulse strains and a last electrical stimulation pulse train of the at least three electrical stimulation pulse trains.

14. The device of claim 9, further comprising an implantable medical lead configured to be coupled to the means for applying the first plurality of electrical stimulation pulse trains and the means for applying the second plurality of electrical stimulation pulse trains.

15. A method comprising:

applying, according to a first delivery cycle, a first plurality of electrical stimulation pulse trains from an electrical stimulation device to a patient, wherein each electrical stimulation pulse train of the first plurality of electrical stimulation pulse trains comprises a series of pulses, wherein the first delivery cycle of the first plurality of electrical stimulation pulse trains is a first ratio of a first time duration during which the electrical stimulation pulse train of the first plurality of electrical stimulation pulse trains is delivered to a second time duration between successive electrical stimulation pulse trains of the first plurality of electrical stimulation pulse trains;

receiving at least one of a user input or physiological information from a physiological information sensing device;

applying, according to a second delivery cycle and in response to the indication of the at least one of the user input or the physiological information, a second plurality of electrical stimulation pulse trains from the electrical stimulation device to the patient, wherein each electrical stimulation pulse train of the second plurality of electrical stimulation pulse trains comprises a series of pulses, wherein the second delivery cycle of the second plurality of electrical stimulation pulse trains is a second ratio of a first time duration during which the electrical stimulation pulse train of the second plurality of electrical stimulation pulse trains is delivered to a second time duration between successive electrical stimulation pulse trains of the second plurality of electrical stimulation pulse trains and is different than the first delivery cycle; and automatically changing, over at least three electrical stimulation pulse trains, the second delivery cycle to a third delivery cycle different than the second delivery cycle, wherein each electrical stimulation pulse train of the at least three electrical stimulation pulse trains comprises a plurality of pulses, and wherein the third delivery cycle is a third ratio of a first time duration during which a final electrical stimulation pulse train of the at least three electrical stimulation pulse trains is delivered to a second time duration between successive electrical stimulation pulse trains of the at least three electrical stimulation pulse trains.

16. The method of claim 15, wherein automatically changing, over at least three electrical stimulation pulse trains, t the second delivery cycle to the third delivery cycle comprises:

at least one of automatically increasing, over the at least three electrical stimulation pulse trains, the delivery cycle of the electrical stimulation pulse train or automatically decreasing, over the at least three electrical stimulation pulse trains, the delivery cycle of the electrical stimulation pulse train.

17. The method of claim 15, wherein the electrical stimulation pulse trains from the electrical stimulation device are applied to at least one of a sacral nerve, a pudendal nerve, or a dorsal genital nerve of the patient to alleviate a pelvic floor disorder of the patient.

18. The method of claim 15, wherein:

applying the first plurality of electrical stimulation pulse trains from the electrical stimulation device to the patient comprises applying the first plurality of electrical stimulation pulse trains from the electrical stimulation device to the patient via an implantable medical lead; and applying the second plurality of electrical stimulation pulse trains from the electrical stimulation device to the patient comprises applying the second plurality of electrical stimulation pulse trains from the electrical stimulation device to the patient via an implantable medical lead.

19. The method of claim 15, wherein the at least one of the user input or the physiological information comprises an indication of a voiding or defecation event.

20. The method of claim 15, wherein a pulse duty cycle is substantially unchanged between a first electrical stimulation pulse train of the at least three electrical stimulation pulse strains and a last electrical stimulation pulse train of the at least three electrical stimulation pulse trains.

21. A non-transitory computer readable medium comprising instructions that cause a one or more processors to:
cause a therapy delivery circuit to apply, according to a first delivery cycle, a first plurality of electrical stimulation pulse trains from an electrical stimulation device to a patient, wherein each electrical stimulation pulse train of the first plurality of electrical stimulation pulse trains comprises a series of pulses, wherein the first delivery cycle of the first plurality of electrical stimulation pulse trains is a first ratio of a first time duration during which the electrical stimulation pulse train of the first plurality of electrical stimulation pulse trains is delivered to a second time duration between successive electrical stimulation pulse trains of the first plurality of electrical stimulation pulse trains;
receive at least one of a user input or physiological information from a physiological information sensing device;
cause the therapy delivery circuit to apply, according to a second delivery cycle and in response to the at least one of the user input or the physiological information, a second plurality of electrical stimulation pulse trains from the electrical stimulation device to the patient, wherein each electrical stimulation pulse train of the second plurality of electrical stimulation pulse trains comprises a series of pulses, wherein the second delivery cycle of the second plurality of electrical stimulation pulse trains is a second ratio of a first time duration during which the electrical stimulation pulse train of the second plurality of electrical stimulation pulse trains is delivered to a second time duration between successive electrical stimulation pulse trains of the second plurality of electrical stimulation pulse trains and is different than the first delivery cycle; and
cause the therapy delivery circuit to automatically change, over at least three electrical stimulation pulse trains, the second delivery cycle to a third delivery cycle different than the second delivery cycle, wherein each electrical stimulation pulse train of the at least three electrical stimulation pulse trains comprises a plurality of pulses, and wherein the third delivery cycle is a third ratio of a first time duration during which a final electrical stimulation pulse train of the at least three electrical stimulation pulse trains is delivered to a second time duration between successive electrical stimulation pulse trains of the at least three electrical stimulation pulse trains.

22. The non-transitory computer readable medium of claim 21, wherein the instructions that cause the one or more processors to cause the therapy delivery circuit to automatically change, over at least three electrical stimulation pulse trains, the delivery cycle of the electrical stimulation pulse trains from the second delivery cycle to a third, different delivery cycle comprise instructions that cause the one or more processors to:
causing the therapy delivery circuit to at least one of automatically increasing, over the at least three electrical stimulation pulse trains, the delivery cycle of the electrical stimulation pulse train or automatically decreasing, over the at least three electrical stimulation pulse trains, the delivery cycle of the electrical stimulation pulse train.

23. The non-transitory computer readable medium of claim 20, wherein a pulse duty cycle is substantially unchanged between a first electrical stimulation pulse train of the at least three electrical stimulation pulse strains and a last electrical stimulation pulse train of the at least three electrical stimulation pulse trains.

* * * * *